(12) United States Patent
Inoue et al.

(10) Patent No.: US 11,685,919 B2
(45) Date of Patent: Jun. 27, 2023

(54) COMPOSITION FOR PREVENTING OR TREATING NEURODEGENERATIVE DISEASE

(71) Applicant: KYOTO UNIVERSITY, Kyoto (JP)

(72) Inventors: Haruhisa Inoue, Kyoto (JP); Koh Ono, Kyoto (JP); Keiko Imamura, Kyoto (JP); Takahiro Horie, Kyoto (JP); Fumiko Nakazeki, Kyoto (JP)

(73) Assignee: Kyoto University, Kyoto (JP)

( * ) Notice: Subject to any disclaimer, the term of this patent is extended or adjusted under 35 U.S.C. 154(b) by 212 days.

(21) Appl. No.: 17/253,484

(22) PCT Filed: Jun. 21, 2019

(86) PCT No.: PCT/JP2019/025759
§ 371 (c)(1),
(2) Date: Mar. 8, 2021

(87) PCT Pub. No.: WO2019/245060
PCT Pub. Date: Dec. 26, 2019

(65) Prior Publication Data
US 2021/0189395 A1    Jun. 24, 2021

(30) Foreign Application Priority Data
Jun. 22, 2018 (JP) .............................. JP2018-119251

(51) Int. Cl.
*C12N 15/113* (2010.01)
*A61P 25/28* (2006.01)

(52) U.S. Cl.
CPC ............ *C12N 15/113* (2013.01); *A61P 25/28* (2018.01); *C12N 2310/113* (2013.01); *C12N 2310/315* (2013.01)

(58) Field of Classification Search
CPC ............ C12N 15/113; C12N 2310/113; C12N 2310/315; A61P 25/28
See application file for complete search history.

(56) References Cited

FOREIGN PATENT DOCUMENTS

WO   WO-2012/027704 A1   3/2012
WO   WO-2013/111081 A1   8/2013

OTHER PUBLICATIONS

Ha M, Kim VN. Regulation of microRNA biogenesis. Nat Rev Mol Cell Biol. Aug. 2014;15(8):509-24. doi: 10.1038/nrm3838. Epub Jul. 16, 2014. PMID: 25027649 (Year: 2014).*
Zempel et al, Amyloid-B oligomers induce synaptic damage via Tau-dependent microtubule severing by TTLL6 and spastin, 2013, EMBO Journal, 32, 2920-2937 (Year: 2013).*
Meyer et al., Early-onset ALS with long-term survival associated with spastin gene mutation, 2005, Neurology, 65, 141-143 (Year: 2005).*
Munch et al., Heterozygous S44L missense change of the spastin gene in amyotrophic lateral sclerosis, 2008, Amyotrophic Lateral Sclerosis, 9, 251-253 (Year: 2008).*
Henson et al., "Transcriptional and Post-Transcriptional Regulation of SPAST, the Gene Most Frequently Mutated in Hereditary Spastic Paraplegia" PLoS One, May 2012, 7(5):e36505, 1-14.
International Search Report dated Aug. 20, 2019 in PCT/JP2019/025759.
Nakazeki et al., "MiR-33a is a therapeutic target in SPG4-related hereditary spastic paraplegia human neurons," Clinical Science, Feb. 2019, 133:583-595.
Jan et al., "Direct intracerebral delivery of a miR-33 antisense oligonucleotide into mouse brain increases brain ABCA1 expression," Neuroscience Letters, May 6, 2015, 598:66-72.
Liao et al., "Effectiveness of a Layer-by-Layer Microbubbles-Based Delivery System for Applying Minoxidil to Enhance Hair Growth," Theranostics, 2016, 6(6):817-827.
Supplementary European Search Report dated Mar. 18, 2022 in EP 19823375.1.

* cited by examiner

*Primary Examiner* — J. E. Angell
*Assistant Examiner* — Keyur A Vyas
(74) *Attorney, Agent, or Firm* — Foley & Lardner LLP

(57) ABSTRACT

An object of the present invention is to provide a therapeutic agent for hereditary spastic paraplegia (HSP) SPG4. Specifically, the present invention relates to a composition for preventing or treating a neurodegenerative disease such as hereditary spastic paraplegia SPG4, the composition comprising, as an active ingredient, a substance that inhibits a function of miR-33a.

3 Claims, 26 Drawing Sheets
(3 of 26 Drawing Sheet(s) Filed in Color)
Specification includes a Sequence Listing.

FIG. 1B premiR-33a without seed sequence
CTGTGGGCGGAACGGCAATTAGTGATAACTTCCGTATAGCCATATACATTATACGAAGTTAT GTTTGTAGTACCATTGTGTTCTAATGGTACCCA TGCAATGTTTCCACAGTGCATCACAG (SEQ ID NO:26)

premiR-33b without seed sequence
GCGGGCGGGCGGAACGGCAATTAGTGATAACTTCCGTATAGCATATACATTATACGAAGTTAT GTTTGTAGTACCATTGCCCCCTGGCACCAC (SEQ ID NO:27)

FIG. 1E

|  | miR-33a KO | miR-33b KO | miR-33 dKO |
|---|---|---|---|
| clone-1 | | | |
| clone-2 | | | |

FIG. 3E

| | |
|---|---|
| Human | A-AAAC-AGACUUAAAC-AAAAUAUA<u>CAAUGCAA</u>AUGUAAUU<br>(SEQ ID NO:30) |
| Chimpanzee | A-AAAC-AAACUUAAAC-AAAAUAUA<u>CAAUGCAA</u>AUGGAAUU<br>(SEQ ID NO:31) |
| Rhesus | A-AAAC-AAACUUAAAC-AAAAUAUA<u>CAAUGCAA</u>AUAGAAUU<br>(SEQ ID NO:32) |
| Dog | A-AAAC-AAAUUAAAU-AAAAUAUA<u>CAAUGCAA</u>AUGGAGUA<br>(SEQ ID NO:33) |
| Cow | A-AAAU-AAAUUAAAU-AAAGUAUA<u>CAAUGCAA</u>AUGGAAUA<br>(SEQ ID NO:34) |
| Mouse | A-AGAC-AGACCUAAAU-AAAAUAUGCAAUAUGAAUGGAA--<br>(SEQ ID NO:35) |
| | * **** ********* ************************ |

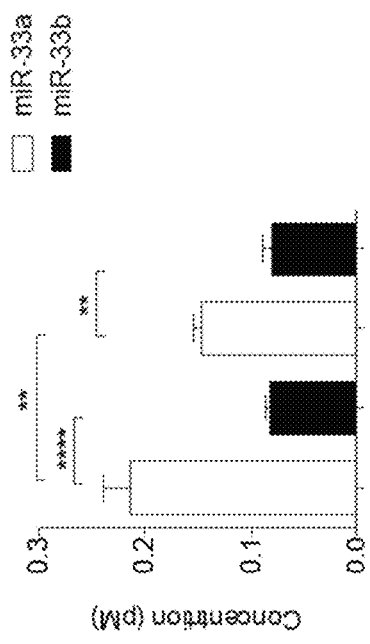
FIG. 8A
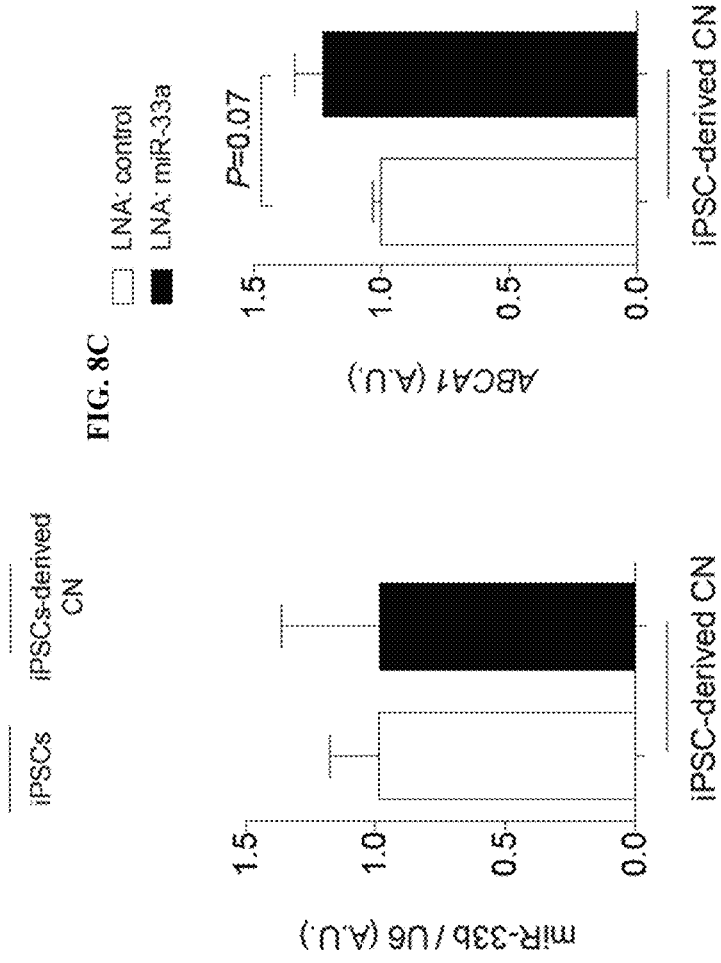
FIG. 8B
FIG. 8C

COMPOSITION FOR PREVENTING OR TREATING NEURODEGENERATIVE DISEASE

CROSS-REFERENCE TO RELATED APPLICATIONS

This application is the U.S. National Stage of PCT/JP2019/025759, filed Jun. 21, 2019, which claims priority to JP 2018-119251, filed Jun. 22, 2018. The instant application contains a Sequence Listing which has been submitted in ASCII format via EFS-WEB and is hereby incorporated by reference in its entirety. Said ASCII copy, created on Dec. 5, 2020, is named sequence.txt and is 7,128 bytes.

Technical Field

The present invention relates to a composition for preventing or treating a neurodegenerative disease such as hereditary spastic paraplegia (HSP) SPG4 (hereinafter, occasionally referred to as "HSP-SPG4").

Background Art

Hereditary spastic paraplegia (HSP) is a neurodegenerative disease characterized by progressive lower leg spastic paralysis due to denaturation of neurites in the corticospinal motor pathway, and HSP is in most cases HSP-SPG4, which involves mutation of the SPAST gene (Non Patent Literature 1). The SPAST gene encodes a microtubule-severing protein called SPASTIN.

Conventional therapeutic methods for HSP-SPG4 are all those of suppressing cell death by mitigating endoplasmic reticulum stress, and there is no direct therapeutic method.

CITATION LIST

Non Patent Literature

Non Patent Literature 1: Henson B. J. et al., PLoS ONE, 2012, Volume 7, Issue 5, e36505

Summary of Invention: In view of the above-described circumstance, an object of the present invention is to provide a composition for preventing or treating a neurodegenerative disease such as HSP-SPG4.

The present inventors diligently studied to solve the above problem, and in the study with human iPS cells whose microRNA (miRNA; miR)-33 has been knocked out, the present inventors searched for a gene that exhibits an increased expression level by using a database, and as a result extracted the SPAST gene. As described above, the SPAST gene has already been known to be a causative gene for HSP-SPG4.

On the other hand, iPS cells were established by using HSP-SPG4 patient-derived cells, and differentiated into neurons. Confirmed was a known phenomenon that there is a mutation (exon 9) in the protein encoded by the SPAST gene (SPASTIN) in HSP-SPG4 patient-derived cells. Induction of differentiation of HSP-SPG4 patient-derived cells into neurons revealed that the neurons had shorter and less branched neurites. Furthermore, suppression of miR-33a with a synthetic DNA oligonucleotide in neurons differentiated from HSP-SPG4 patient-derived cells resulted in the increase of the SPASTIN level and amelioration of the shortening of neuronal axons due to HSP-SPG4. Thus, the present inventors found that HSP-SPG4 can be directly treated through suppression of miR-33a, completing the present invention.

Specifically, the present invention includes the followings.

(1) An miR-33a function inhibitor comprising, as an active ingredient, a substance that inhibits a function of miR-33a.

(2) A composition for preventing or treating a neurodegenerative disease, the composition comprising, as an active ingredient, a substance that inhibits a function of miR-33a.

(3) The composition for preventing or treating according to (2), wherein the neurodegenerative disease is HSP-SPG4.

(4) The miR-33a function inhibitor or composition for preventing or treating a neurodegenerative disease according to any one of (1) to (3), wherein the substance that inhibits a function of miR-33a is a nucleic acid that inhibits a function of miR-33a.

(5) The miR-33a function inhibitor or composition for preventing or treating a neurodegenerative disease according to (4), wherein the nucleic acid that inhibits a function of miR-33a is an antisense oligonucleotide that hybridizes with miR-33a and inhibits a function of miR-33a.

(6) The miR-33a function inhibitor or composition for preventing or treating a neurodegenerative disease according to (5), wherein the antisense oligonucleotide consists of a complementary strand of a nucleotide sequence set forth in SEQ ID NO: 1 or a nucleotide sequence of 12 or more consecutive nucleotides therein.

(7) The miR-33a function inhibitor or composition for preventing or treating a neurodegenerative disease according to (6), wherein the antisense oligonucleotide consists of a nucleotide sequence set forth in SEQ ID NO: 24, and each internucleotide bond in the nucleotide sequence is a phosphorothioate bond.

(8) A method for preventing or treating a neurodegenerative disease, the method comprising administering a substance that inhibits a function of miR-33a to a subject.

(9) The method according to (8), wherein the neurodegenerative disease is HSP-SPG4.

(10) The method according to (8) or (9), wherein the substance that inhibits a function of miR-33a is a nucleic acid that inhibits a function of miR-33a.

(11) The method according to (10), wherein the nucleic acid that inhibits a function of miR-33a is an antisense oligonucleotide that hybridizes with miR-33a and inhibits a function of miR-33a.

(12) The method according to (11), wherein the antisense oligonucleotide consists of a complementary strand of a nucleotide sequence set forth in SEQ ID NO: 1 or a nucleotide sequence of 12 or more consecutive nucleotides therein.

(13) The method according to (12), wherein the antisense oligonucleotide consists of a nucleotide sequence set forth in SEQ ID NO: 24, and each internucleotide bond in the nucleotide sequence is a phosphorothioate bond.

(14) Use of a substance that inhibits a function of miR-33a in manufacture of a medicament for preventing or treating a neurodegenerative disease.

(15) The use according to (14), wherein the neurodegenerative disease is HSP-SPG4.

(16) The use according to (14) or (15), wherein the substance that inhibits a function of miR-33a is a nucleic acid that inhibits a function of miR-33a.

(17) The use according to (16), wherein the nucleic acid that inhibits a function of miR-33a is an antisense oligonucleotide that hybridizes with miR-33a and inhibits a function of miR-33a.

(18) The use according to (17), wherein the antisense oligonucleotide consists of a complementary strand of a nucleotide sequence set forth in SEQ ID NO: 1 or a nucleotide sequence of 12 or more consecutive nucleotides therein.

(19) The use according to (18), wherein the antisense oligonucleotide consists of a nucleotide sequence set forth in SEQ ID NO: 24, and each internucleotide bond in the nucleotide sequence is a phosphorothioate bond.

(20) A substance that inhibits a function of miR-33a for use in preventing or treating a neurodegenerative disease.

(21) The substance according to (20), wherein the neurodegenerative disease is HSP-SPG4.

(22) The substance according to (20) or (21), wherein the substance that inhibits a function of miR-33a is a nucleic acid that inhibits a function of miR-33a.

(23) The substance according to (22), wherein the nucleic acid that inhibits a function of miR-33a is an antisense oligonucleotide that hybridizes with miR-33a and inhibits a function of miR-33a.

(24) The substance according to (23), wherein the antisense oligonucleotide consists of a complementary strand of a nucleotide sequence set forth in SEQ ID NO: 1 or a nucleotide sequence of 12 or more consecutive nucleotides therein.

(25) The substance according to (24), wherein the antisense oligonucleotide consists of a nucleotide sequence set forth in SEQ ID NO: 24, and each internucleotide bond in the nucleotide sequence is a phosphorothioate bond.

The present specification includes the contents disclosed in Japanese Patent Application No. 2018-119251, on which priority of the present application is based.

BRIEF DESCRIPTION OF DRAWINGS

The application file contains at least one drawing executed in color. Copies of this patent application publication with color drawing(s) will be provided by the Office upon request and payment of the necessary fee.

FIG. 1B shows that DNA sequencing confirmed the deletions and insertions generated by CRISPR-Cas9. Each loxP sequenced is highlighted by an underline. FIG. 1E shows karyotype analysis in miR-33 KO iPSCs.

FIG. 1B shows continuation from FIG. 1A.
FIG. 1C shows continuation from FIG. 1B.
FIG. 1D shows continuation from FIG. 1C.
FIG. 1E shows continuation from FIG. 1D.

FIG. 2A shows schematic structures of the miR-33 locus and DNA cleavage sites. FIG. 2B shows that expression levels of mature miR-33 were normalized by that of U6 small nuclear RNA. n=3 in each clone, two clones per each knockout line. ****$P<0.0001$ by one-way ANOVA. FIG. 2C shows protein levels of host genes in miR-33 KO iPSCs. Two clones per each knockout line. FIG. 2D shows that sequencing at the junction between exons 16 and 17 of SREBF2 mRNA and that between exons 17 and 18 of SREBF1 indicated the achievement of correct splicing.

FIG. 2B shows continuation from FIG. 2A.
FIG. 2C shows continuation from FIG. 2B.
FIG. 2D shows continuation from FIG. 2C.

FIGS. 3A-3G demonstrate that expression levels of SPAST were up-regulated in all miR-33 KO iPSCs. FIG. 3A shows an MA plot (M, log ratio; A, average) of miR-33 KO iPSCs versus a control [fold change (FC)>2 was highlighted with a parenthesis]. FIG. 3B shows a Venn diagram, which displayed overlaps between up-regulated genes in each KO iPSCs and top 200 predicted targets of miR-33 by TargetScan. FIG. 3C shows validation of SPAST induced by deficiency of miR-33. n=3 in each clone, two clones per each knockout line. $P<0.01$, *$P<0.001$ by one-way ANOVA. FIG. 3D shows protein levels of SPASTIN in miR-33 KO iPSCs. Two clones per each knockout line, two independent experiments. FIG. 3E shows conservation of miR-33 target regions in the 3'-UTR of SPAST. Underlined sequences are each a potential binding site of miR-33 seed sequences. * indicated the conservation among species. FIG. 3F shows 3'-UTR reporter assay used to verify the target. Luciferase reporter activity of human SPAST gene 3'-UTR constructs in HEK293T cells overexpressing miR-control (miR-C) and miR-33 (n=6 each, **$P<0.0001$ by unpaired t-test). FIG. 3G shows luciferase reporter activity of the WT or mutant SPAST 3'-UTR at the potential miR-33 binding site in HEK293T cells (n=6 each, *$P<0.01$, ****$P<0.0001$ by unpaired t-test).

FIGS. 3B and 3C show continuation from FIG. 3A.
FIG. 3D shows continuation from FIGS. 3B and 3C.
FIG. 3E shows continuation from FIG. 3D.
FIGS. 3F and 3G show continuation from FIG. 3E.

FIG. 4A shows the pedigree of an SPG4 patient in Example. FIG. 4B shows sequencing for the presence of the heterozygous SPG4 mutation IVS9+1 G→A. FIG. 4C shows expression levels of SPAST in iPSC-derived cortical neurons. n=5 for SPG4, n=4 to 5 each for controls, two clones per control line. *$P<0.001$ by unpaired t-test. FIG. 4D shows protein levels of SPASTIN in iPSC-derived cortical neurons. n=3 for SPG4, n=2 each in controls. *$P<0.001$ by unpaired t-test. FIG. 4E shows representative immunofluorescent staining of β3-tubulin (green). Nuclei are labeled with DAPI (white). Neurite length from SPG4-derived cortical neurons is compared with that from control neurons. Images were automatically captured by using a Cellomics ArrayScanVTI. By using a 10× objective, a sufficient number of fields (>30) were acquired for the analysis of at least 50 cells per field. *$P<0.05$, **$P<0.01$ by unpaired t-test.

FIGS. 4C and 4D show continuation from FIGS. 4A and 4B.

FIG. 4E shows continuation from FIGS. 4C and 4D.

FIG. 7A shows representative images of transfected SPG4-derived neurons, labeled with GFP. Neurite tracings are shown in black inserts. Scale bars: 100 µm. FIG. 7B shows the total neurite length in GFP+ SPG4-derived neurons, transfected with the indicated lentivirus. Images were automatically captured by using a Cellomics ArrayScanVTI. By using a 10× objective, a sufficient number of fields (>50) were acquired for the analysis of at least one cell per field. *P>0.05 by one-way ANOVA.

FIG. 7B shows continuation from FIG. 7A.

FIG. 8A shows absolute levels of miR-33a and miR-33b at both undifferentiated state and neural differentiation. n=3 to 4 in each clone. P<0.01, P<0.0001 by unpaired t-test. FIG. 8B shows expression levels of miR-33a/b with LNA treatment in iPSC-derived cortical neurons. n=4 to 5 each, P<0.01 by unpaired t-test. FIG. 8C shows expression levels of ABCA1 with LNA treatment in iPSC-derived cortical neurons. n=4 to 5 each.

FIG. 9A shows representative immunofluorescent staining of β3-tubulin (green). SPG4-derived neurons were treated with LNA-control or LNA-miR-33a for 48 hours. FIG. 9B shows the total neurite length in SPG4-derived neurons with LNA treatment. By using a 10× objective, a sufficient number of fields (>30) were acquired for the analysis of at least 50 cells per field. ***P>0.001 by one-way ANOVA.

FIGS. 10C and 10D show continuation from FIGS. 10A and 10B.

FIG. 10E shows continuation from FIGS. 10C and 10D.

DESCRIPTION OF EMBODIMENTS

Figure 1A:
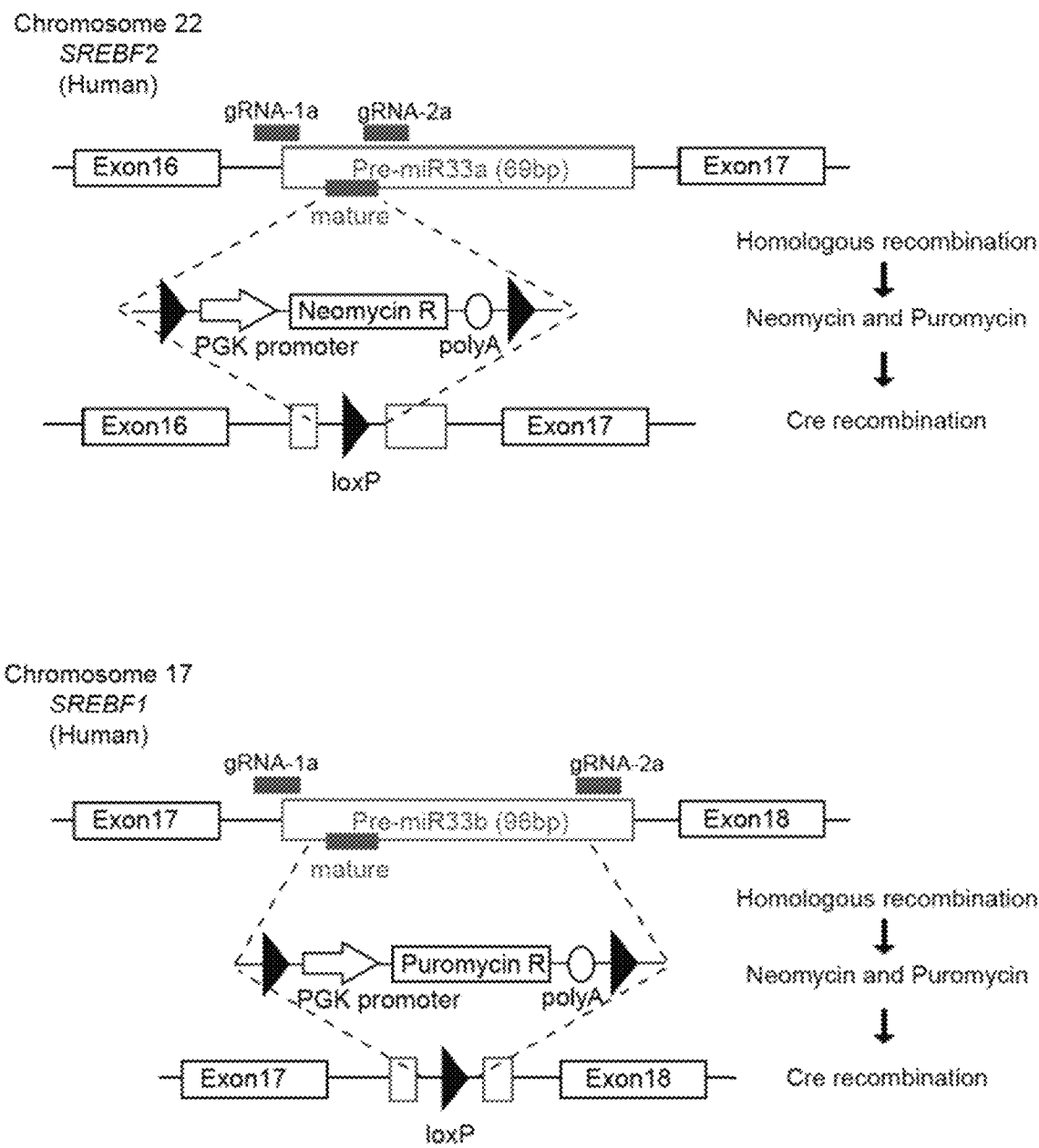
FIG. 1A shows a schematic diagram of human SREBF2 and SREBF1 loci with targeting strategy. The donor template was designed to have a PGK-Neomycin and/or Puromycin selection cassette flanked by two loxP sites and homology arms. PGK promoter: phosphoglycerol kinase promoter, Neomycin R: neomycin resistance gene, Puromycin R: puromycin resistance gene, polyA: polyadenylation sequence.

Hereinafter, the present invention will be described in detail.

The miR-33a function inhibitor according to the present invention comprises, as an active ingredient, a substance that inhibits a function of miR-33a. The miR-33a function inhibitor according to the present invention can increase the expression of the protein SPASTIN encoded by the SPAST gene to ameliorate symptoms of HSP-SPG4 (e.g., the shortening of neuronal axons) through suppressing binding of miR-33a to an miR-33 binding site present in the 3'-UTR of mRNA transcribed from the SPAST gene, a causative gene for HSP-SPG4. In other words, the miR-33a function inhibitor according to the present invention is a composition for preventing or treating a neurodegenerative disease such as HSP-SPG4. In the following, the miR-33a function inhibitor and composition for preventing or treating a neurodegenerative disease according to the present invention are occasionally referred to as "the drug according to the present invention" in a collective manner.

Here, a function of miR-33a means binding to an miR-33 binding site present in the 3'-UTR of mRNA transcribed from the SPAST gene to inhibit the translation of the mRNA into protein, or suppressing the expression of the SPAST gene through inducing degradation of the mRNA.

The neurodegenerative disease that can be prevented or treated by the drug according to the present invention is not particularly limited and may be any neurodegenerative disease caused by miR-33a, and is preferably HSP-SPG4.

The substance that inhibits a function of miR-33a, as an active ingredient of the drug according to the present invention is not particularly limited and may be any substance capable of inhibiting a function of miR-33a, and is preferably a nucleic acid that inhibits a function of miR-33a.

The nucleic acid that inhibits the function of miR-33a is not particularly limited and may be any nucleic acid that hybridizes with miR-33a and inhibits a function of miR-33a, and is preferably an antisense oligonucleotide to miR-33a. The antisense oligonucleotide to miR-33a reduces miR-33a levels or inhibits a function of miR-33a through hybridization of miR-33a and a strand complementary to at least a partial sequence of miR-33a possessed by the antisense oligonucleotide.

miRNA (miR) is single-stranded non-coding RNA with a length of 20 to 25 nucleotides. First, miRNA is transcribed from DNA into single-stranded pri-miRNA including miRNA and a complementary strand thereto and being capable of forming a hairpin loop structure. Subsequently, pri-miRNA is partially cleaved by an enzyme called Drosha present in nuclei to become pre-miRNA, which is extranuclearly transported. Thereafter, pre-miRNA is further cleaved by Dicer to become mature miRNA.

The antisense oligonucleotide to miR-33a can be chemically synthesized through a known procedure on the basis of the nucleotide sequence of human mature miR-33a (SEQ ID NO: 1). The antisense oligonucleotide to miR-33a preferably includes a complementary strand of the nucleotide sequence of human mature miR-33a set forth in SEQ ID NO: 1 or a partial sequence thereof (e.g., a nucleotide sequence of 12 or more consecutive nucleotides, such as 12 to 20 consecutive nucleotides, including a seed sequence), or consists of the complementary strand or a partial sequence thereof.

The antisense oligonucleotide to miR-33a may include, for example, a nucleotide sequence hybridizable to a nucleotide sequence consisting of 1st to 21st nucleotides, preferably of 2nd to 13th nucleotides, in the nucleotide sequence of human mature miR-33a set forth in SEQ ID NO: 1.

Moreover, it is not necessarily needed for the antisense oligonucleotide to miR-33a to include a nucleotide sequence completely complementary to at least a part of the nucleotide sequence of human mature miR-33a set forth in SEQ ID NO: 1, and it is adequate for the antisense oligonucleotide to miR-33a to include a nucleotide sequence with at least 70% of complementarity, preferably with at least 80% of complementarity, more preferably with at least 90% of complementarity, even more preferably with at least 95% of complementarity.

The antisense oligonucleotide to miR-33a may be a nucleic acid that includes a nucleotide sequence that hybridizes with miR-33a under stringent conditions and inhibits a function of miR-33a. "Stringent conditions" refer to, for example, such conditions that incubation is performed in a solution containing 6×SSC (composition of 1×SSC: 0.15 M NaCl, 0.015 M sodium citrate, pH 7.0), 0.5% SDS, 5×Denhardt's solution, 100 µg/mL modified salmon sperm DNA, and 50% (v/v) formamide at room temperature for 12 hours, and washing is further performed with 0.5×SSC at a temperature of 50° C. or higher. Moreover, more stringent conditions (e.g., incubation at 45° C. or 60° C. for 12 hours, washing with 0.2×SSC or 0.1×SSC, washing at a washing temperature of 60° C. or 65° C. or higher) may be used.

The antisense oligonucleotide may be DNA or RNA, or a DNA/RNA chimera.

The nucleotide molecule constituting the antisense oligonucleotide may be naturally-occurring DNA or RNA. The nucleotide molecule can include various chemical modifications to enhance the stability (chemical stability and/or stability against enzymes) or the specific activity (affinity with RNA). To prevent degradation by hydrolase such as nuclease, for example, the phosphate residue (phosphate) of each nucleotide constituting the antisense oligonucleotide can be substituted with a chemically modified phosphate residue such as phosphorothioate, methylphosphonate, and phosphorodithionate. The hydroxy group at position 2' of the sugar (ribose) of each nucleotide may be substituted with —OR (e.g., R=$CH_3$(2'-O-Me), $CH_2CH_2OCH_3$(2'-O-MOE), $CH_2CH_2NHC(NH)NH_2$, $CH_2CONHCH_3$, $CH_2CH_2CN$). Moreover, the base moiety (pyrimidine, purine) may be subjected to chemical modification. Examples of such chemical modification include introduction of a methyl group or a cationic functional group into position 5 of the pyrimidine base, and substitution of the carbonyl group at position 2 of the pyrimidine base with thiocarbonyl.

Two conformations, C2'-endo (S-form) and C3'-endo (N-form), are dominant as the conformation of the sugar part of RNA, and single-stranded RNA exists in equilibrium of the two conformations, and the conformation is fixed to the N-form on forming a double strand. Therefore, BNA (Bridged Nucleic Acid) is preferably used to impart strong binding ability to miR-33a. BNA is an RNA derivative in which the conformation of the sugar part is fixed to the N-form through crosslinking between 2'-oxygen and 4'-carbon. Examples of BNA include 2',4'-BNA (also referred to as LNA (Locked Nucleic Acid)), in which 2'-oxygen and 4'-carbon are crosslinked via methylene, and ENA, in which 2'-oxygen and 4'-carbon are crosslinked via ethylene.

In the antisense oligonucleotide to miR-33a, for example, 2',4'-BNA (LNA) is disposed at 9th, 11th, 13th, 15th, 17th, and/or 19th position(s) in the direction from the 5' side to the 3' side of a complementary strand of the nucleotide sequence of human mature miR-33a set forth in SEQ ID NO: 1.

A specific antisense oligonucleotide to miR-33a is "LNA-anti-miR-33" (SEQ ID NO: 24), which was used in Example below. LNA-anti-miR-33 is a nucleic acid corresponding to a complementary strand of a nucleotide sequence consisting of 2nd to 13th nucleotides in the nucleotide sequence of human mature miR-33a set forth in SEQ ID NO: 1, wherein LNA is disposed at 9th, 11th, 13th, 15th, 17th, and 19th positions in the direction from the 5' side to the 3' side of a complementary strand of the nucleotide sequence of human mature miR-33a set forth in SEQ ID NO: 1, and each internucleotide bond is a phosphorothioate bond.

The drug according to the present invention can be administered orally or parenterally (e.g., intravenously, with subcutaneous or intramuscular injection, topically, intrarectally, transdermally, intraspinally, or nasally). Examples of dosage forms for oral administration include tablets, capsules, pills, granules, powders, liquids, and suspensions. Examples of dosage forms for parenteral administration include aqueous agents for injection, oily agents for injection, ointments, creams, lotions, aerosols, suppositories, and patches. These formulations can be prepared by using a conventionally known technique, and can contain a pharmaceutically acceptable carrier or excipient.

Examples of subjects to which the drug according to the present invention is administered include mammals such as humans, chimpanzees, rhesus macaques, dogs, and cows. The drug according to the present invention is preferably used for humans.

In the case that the active ingredient of the drug according to the present invention is an antisense oligonucleotide to miR-33a and the drug according to the present invention is administered to a human, for example, the active ingredient of the drug according to the present invention is used in such a manner that 120 to 240 µg/kg body weight of the antisense oligonucleotide to miR-33a is administered per day, though the dose depends on the purpose of administration, method of administration, and condition of a subject of administration (e.g., sex, age, body weight, disease state).

In accordance with the above-described drug according to the present invention, the present invention relates to:

a method for preventing or treating a neurodegenerative disease such as HSP-SPG4, the method comprising administering a substance that inhibits a function of miR-33a to a subject;

use of a substance that inhibits a function of miR-33a in manufacture of a medicament for preventing or treating a neurodegenerative disease such as HSP-SPG4; and a substance that inhibits a function of miR-33a for use in preventing or treating a neurodegenerative disease such as HSP-SPG4.

Example

Hereinafter, the present invention will be described in more detail with reference to Example; however, the technical scope of the present invention is not limited to this Example.

[Identification of miR-33a as Therapeutic Target for SPG4 Hereditary Spastic Paraplegia by Using CRISPR-Cas9 Genome Editing in Human Induced Pluripotent Stem Cells (iPSCs)]

1. Introduction microRNAs (miRNAs) are small non-protein-coding RNAs that bind to specific mRNAs and inhibit translation or promote mRNA degradation. miRNAs show cell-type-, tissue-, and species-specific regulation of their targets in different cellular contexts. Therefore, it is critical to study miRNA function in appropriate cell-type, tissue, and species. Previously, the present inventors demonstrated that miR-33 controls lipid homeostasis by using miR-33-deficient mice. However, the physiological functions of miR-33 in humans are still unknown because of lack of appropriate models.

miR-33 has two isoforms: miR-33a and miR-33b. Although miR-33a and miR-33b differ by only two nucleotides in the mature form, they are identical in their seed sequence. miR-33a has been highly conserved throughout evolution, whereas miR-33b is present only in the SREBF1 gene of large mammals, and rodents lack miR-33b.

To investigate novel target genes of miR-33a/b in humans, the present inventors generated miR-33 single (miR-33a or miR-33b) and double (miR-33a and miR-33b) knockout human iPSCs by the CRISPR-Cas9 technology, and analyzed their transcriptomes.

In this Example, the present inventors revealed that SPAST was a novel target gene of miR-33 in humans. Actually, the miR-33 binding site in SPAST 3'-UTR is conserved not in mice but in mid to large mammals, and it is impossible to clarify the roles of miR-33a and miR-33b on SPAST in mice. SPAST encodes a microtubule-severing protein called SPASTIN, and mutations in the SPAST (previously known as "SPG4") gene are the most common causes of hereditary spastic paraplegia (HSP-SPG4). The present inventors demonstrated that miR-33a affected the pathological phenotypes though regulating SPAST expression in SPG4 patient iPSC-derived cortical neurons. Moreover, inhibition of miR-33a, a major form of miR-33 in human neurons, via locked nucleic acid (LNA)-anti-miR ameliorated the pathological phenotype in HSP-SPG4 patient neurons. Thus, miR-33a can be a therapeutic target for treatment of HSP-SPG4.

2. Results 2-1. Generation of miR-33 Knockout Human iPSCs

To investigate the role of miR-33 in human cells, the present inventors generated miR-33 single knockout (KO) and miR-33 double KO cells from human iPSCs.

The present inventors constructed a pair of CRISPR guide RNA (gRNA) expression vectors (Table 1), and co-electroporated them into control iPSCs (named "201B7") together with D10A Cas9 nickase (Cas9n) for introducing a double-strand break.

TABLE 1

Table 1. Sequences of gene targeting strategy
Selected sequences for gene targeting
of CRISPR-Cas9n are shown.

| | Gene targeting sequence |
|---|---|
| miR-33a KO gRNA-1a | GCTGCCCGCCAGGAGGTATGCGG (SEQ ID NO: 2) |
| miR-33a KO gRNA-2a | TGTAGTTGCATTGCATGTTCTGG (SEQ ID NO: 3) |
| miR-33b KO gRNA-1b | TGCAACAGCAATGCACCGCG (SEQ ID NO: 4) |
| miR-33b KO gRNA-2b | TCGGCAGTGCAGCCCGGAGC (SEQ ID NO: 5) |

The double-nicking approach was chosen to minimize off-target mutagenesis. Previous studies showed that the miRNA seed region is the most preferred cleavage site to knockout miRNA genes with high efficiency and specificity, and the present inventors triggered the PAMs (NGG) within/adjacent to each seed region. To facilitate the screening for bi-allelic deletion, the present inventors combined the above procedure with homologous recombination donor vectors, which enabled neomycin- and/or puromycin-resistant selection (FIG. 1A).

Figure 2A:
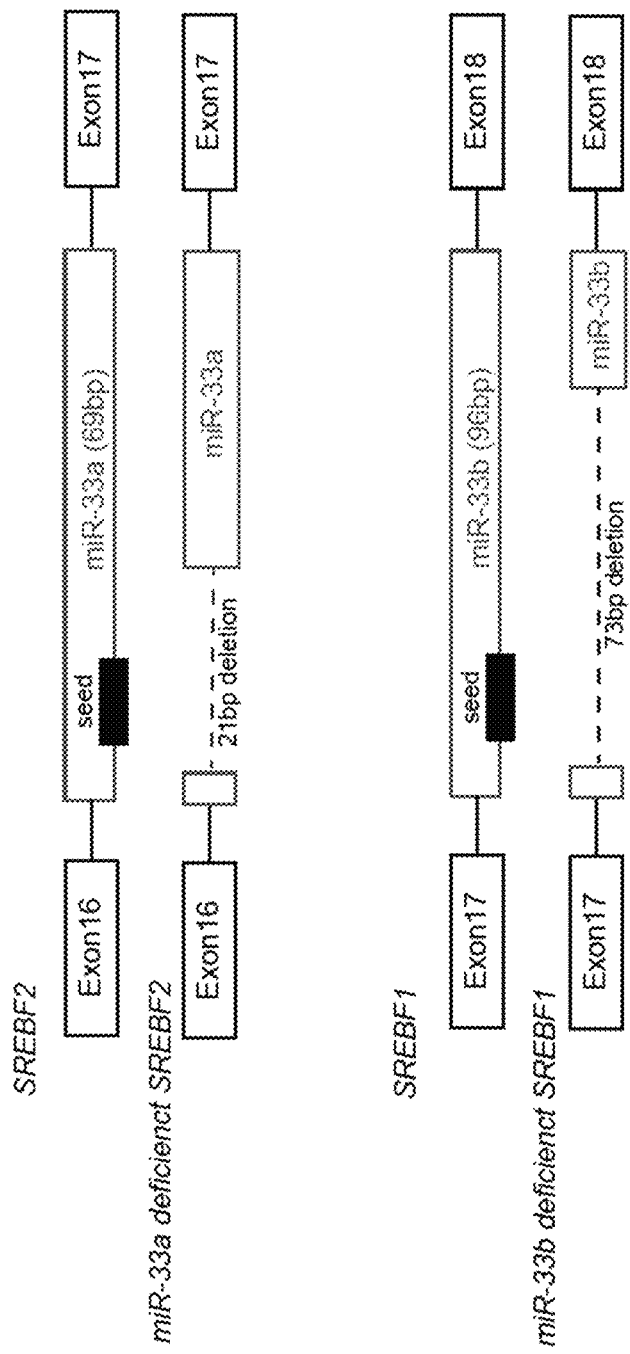
FIGS. 2A-2D demonstrate that CRISPR-Cas9 can significantly down-regulate the expression of miR-33.
Figure 2B:
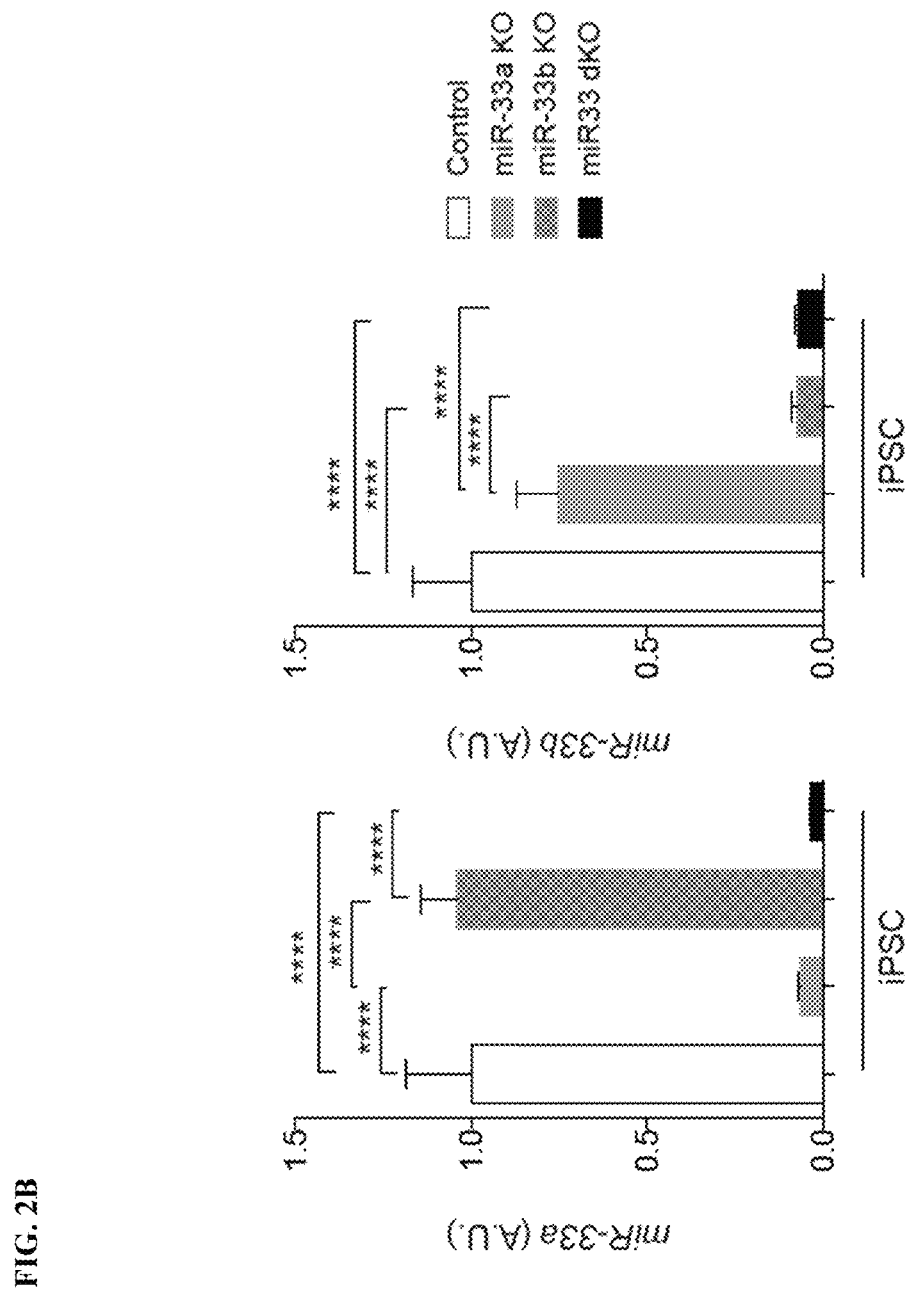
Figure 2C:
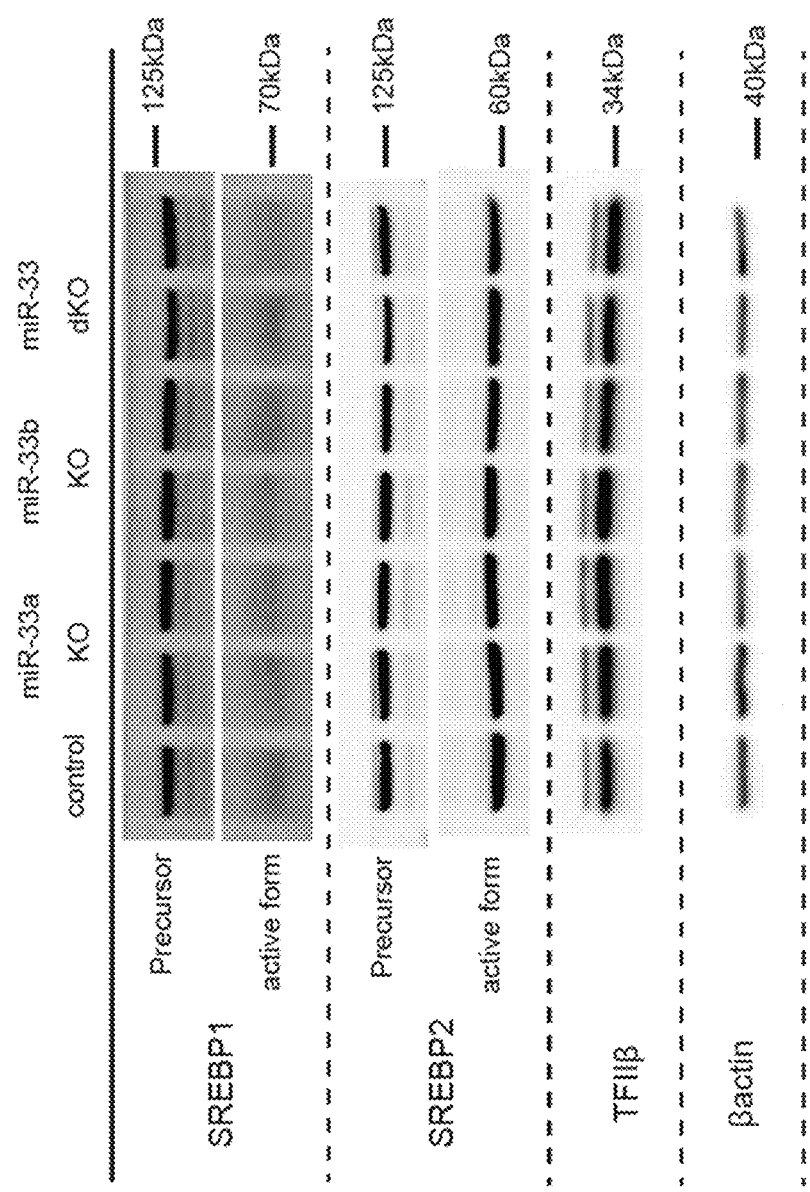
Figure 2D:
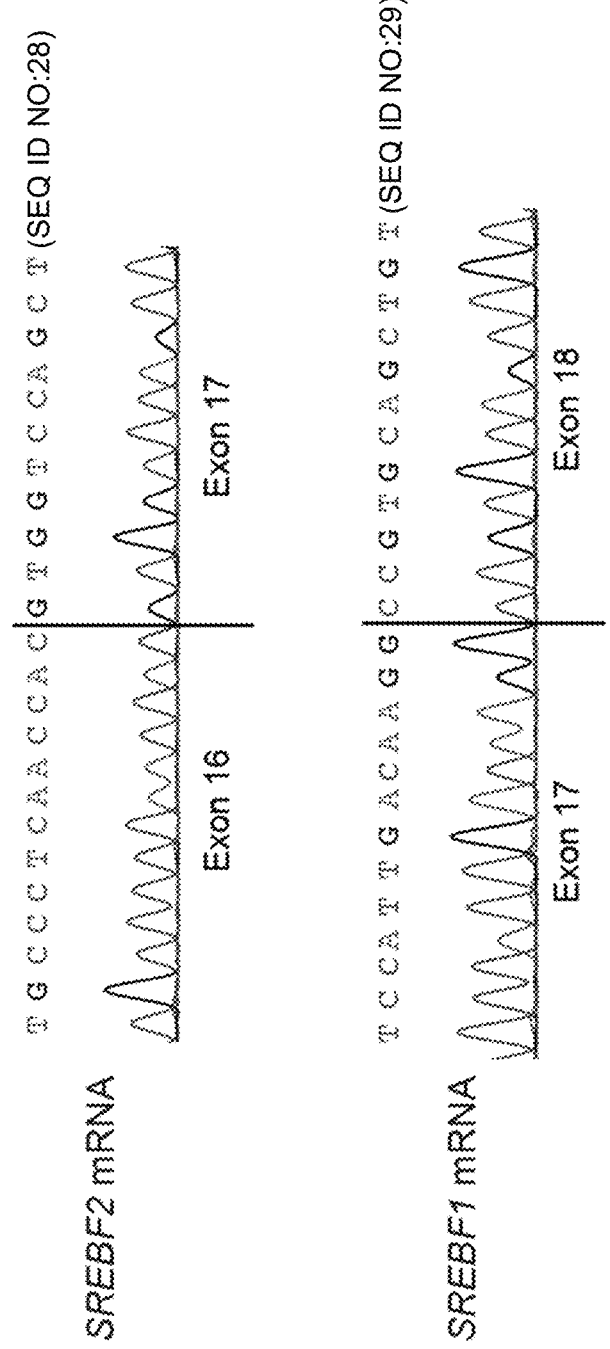

The predicted sizes of indels, such as mature miR-33 sequence deletion and loxP sequence insertion, were identified by DNA sequencing (FIG. 1B and FIG. 2A). Complete loss of miR-33a/b expression in KO iPSCs was confirmed by RT-PCR analysis (FIG. 2B), though slight signals were remained because of the PCR-based miRNA measurement. Deletion of miR-33a and/or miR-33b, encoded by introns of SREBF2 and SREBFJ, did not affect protein levels of their host genes and splicing (FIGS. 2C and 2D).

Figure 1C:
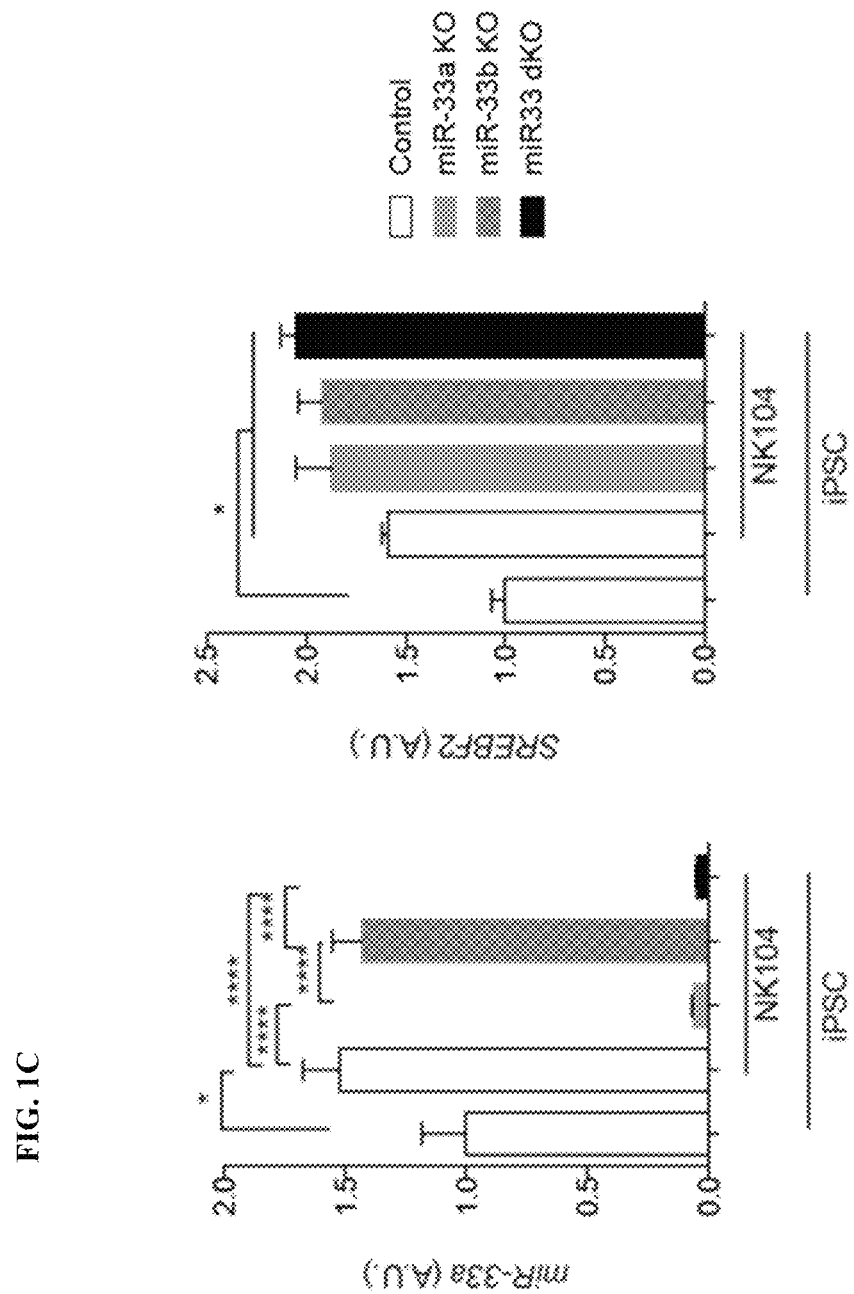
FIG. 1C shows expression levels of mature miR-33a and the host gene (SERBF2) with treatment. n=3 in each clone, two clones per each knockout line. *$P<0.05$, ****$P<0.0001$ by one-way ANOVA.
Figure 1D:
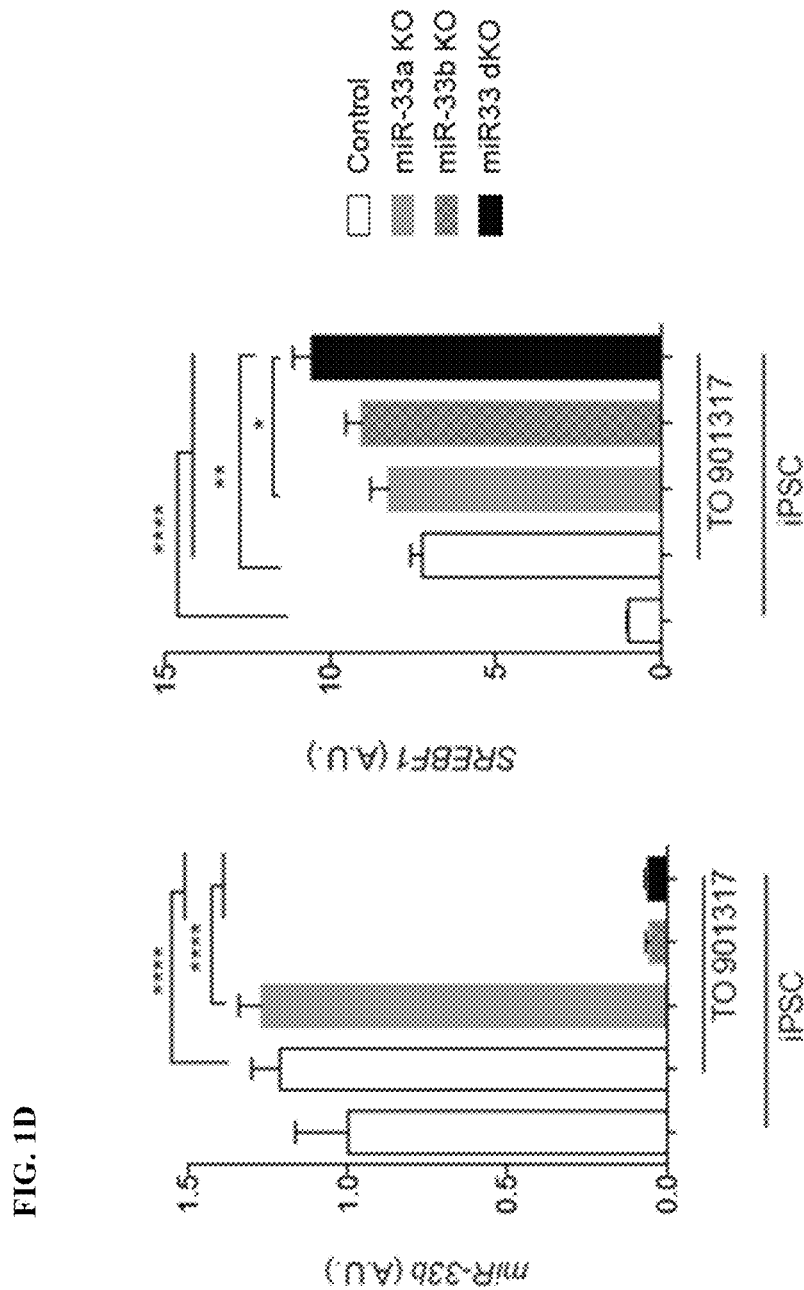
FIG. 1D shows expression levels of mature miR-33b and the host gene (SERBF1) with treatment. n=3 in each clone, two clones per each knockout line. *$P<0.05$, $P<0.01$, **$P<0.0001$ by one-way ANOVA.

The present inventors further attempted to confirm whether the deletion of miR-33 was established without interfering the activation of their host genes. NK104, an HMG-CoA inhibitor, activates the transcription of SREBF2, and TO90137, an LXR agonist, enhances SREBF1 expression. The amounts of SREBF2 and SREBF1 mRNAs in control and KO iPSCs were significantly increased with these pharmacological stimulations, and expression levels of miR-33a/b in control iPSCs were increased in parallel. Because expression levels of miR-33a and/or miR-33b in each KO iPSCs were undetectable even with the stimulations of their host genes, complete loss of miR-33a and/or miR-33b was achieved in miR-33 single and double KO iPSCs (FIGS. 1C and 1D).

Chromosomal Q-band analyses showed that the established iPS lines had normal karyotypes (FIG. 1E).

2-2. miR-33 Regulates SPAST Expression in Humans

Figure 3A:
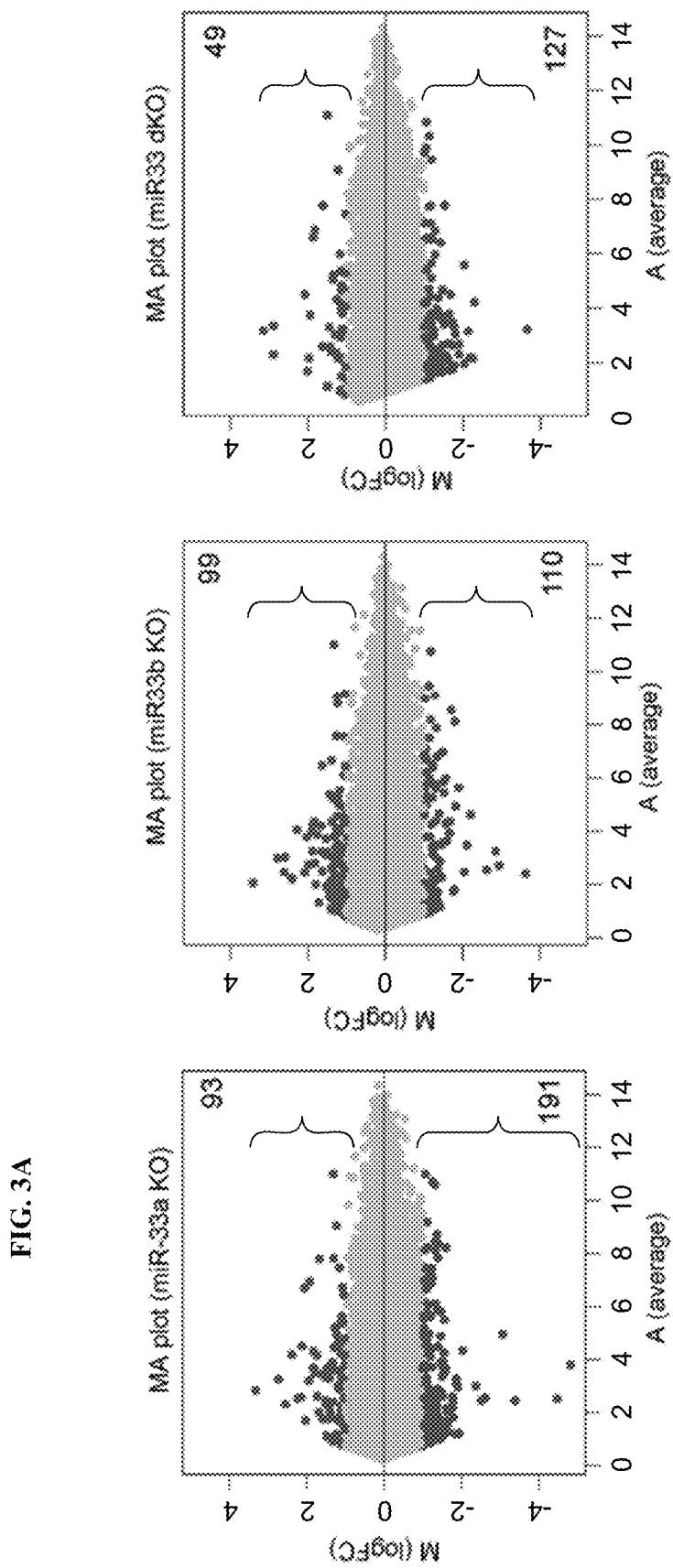

To analyze the effect of miR-33 on human cells, the present inventors performed microarray analysis using miR-33 single and double KO, and control iPSCs (201B7). Detected from the microarray data were 93 up-regulated genes and 191 down-regulated genes in miR-33a KO, 99 up-regulated genes and 110 down-regulated genes in miR-33b KO, and 49 up-regulated genes and 127 down-regulated genes in miR-33 double KO iPSCs versus the control (fold change >2) (FIG. 3A).

Figures 3B, 3C:
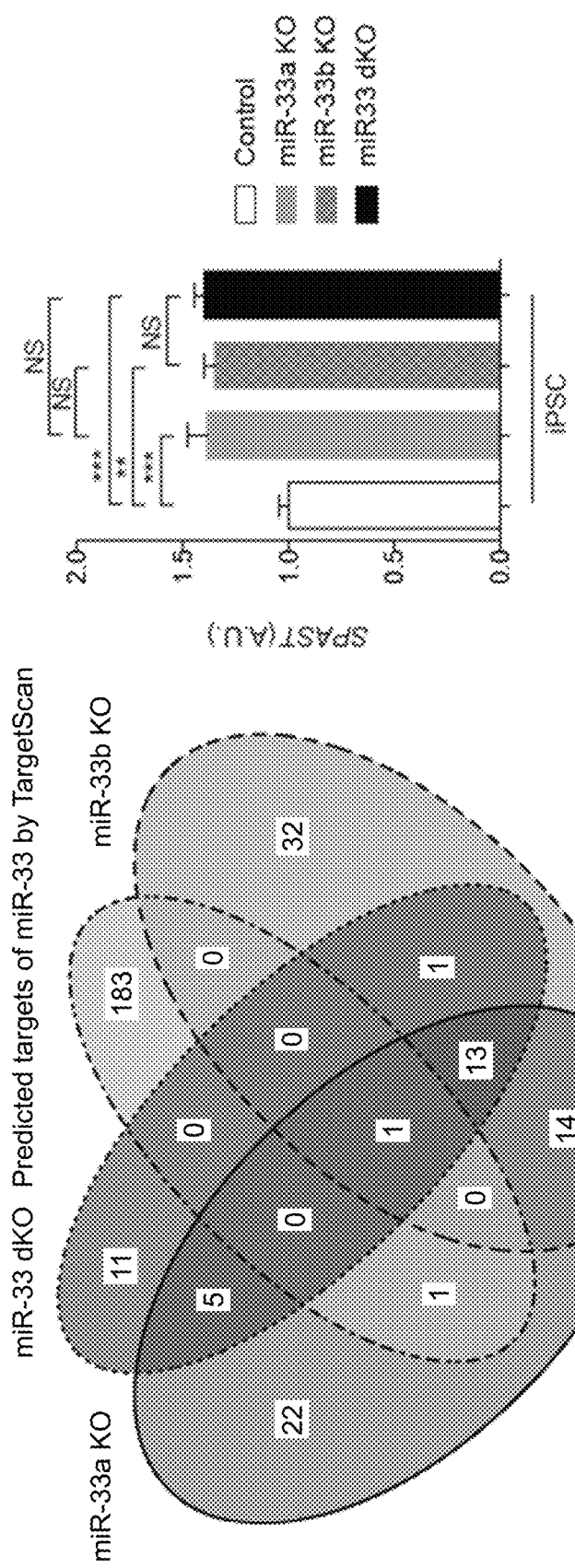

The present inventors searched for the miR-33 target genes among the up-regulated genes in all of the miR-33 single and double KO iPSCs by using the public database TargetScan (www.targetscan.org). As shown in FIG. 3B, SPAST was only one gene identified by this method.

Figure 3D:
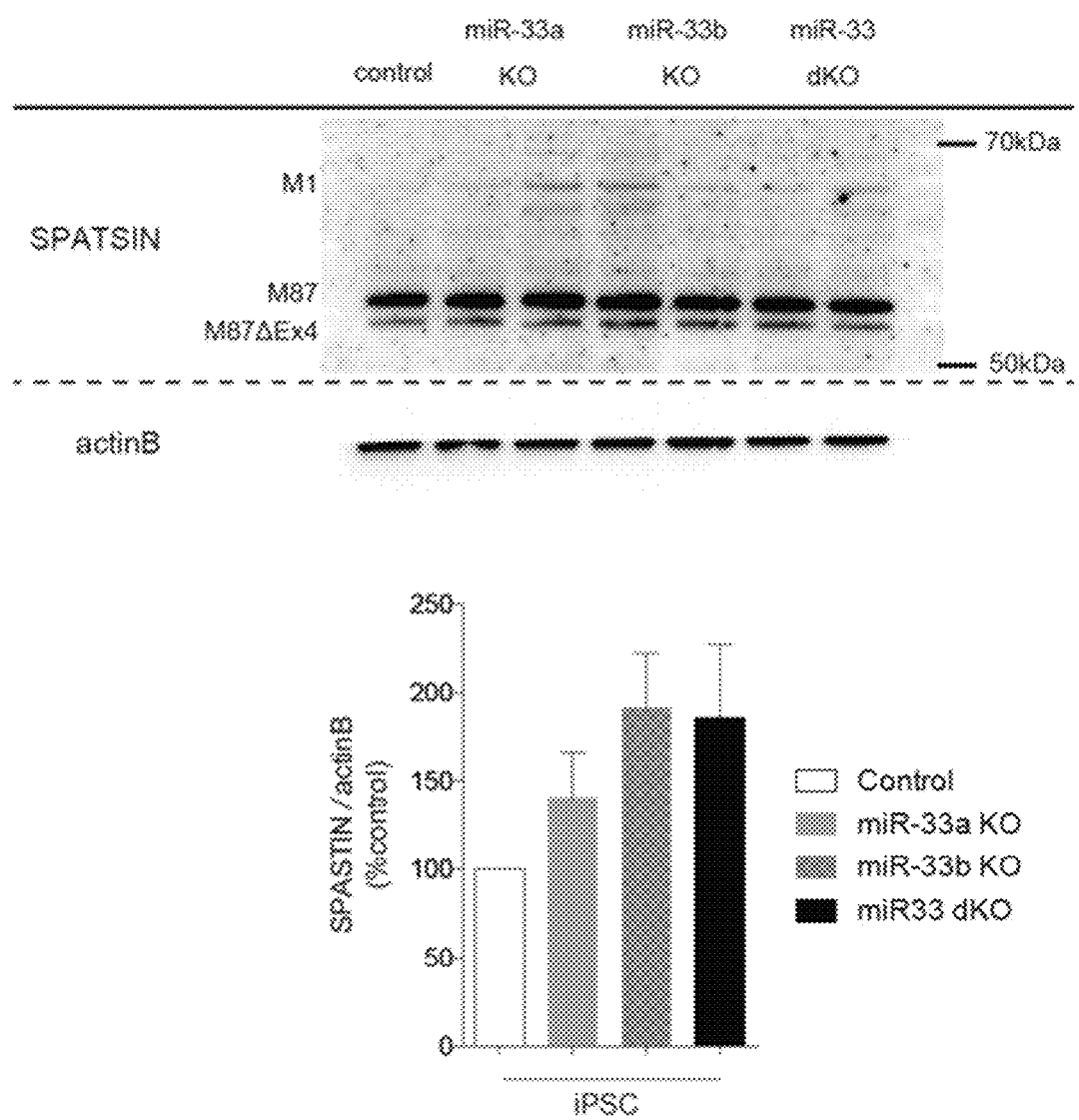

Next, we validated SPAST and SPASTIN expression levels by RT-PCR and Western blotting analysis (FIGS. 3C and 3D). The presence of two translation initiation codons in SPAST allows synthesis of two SPASTIN isoforms: a full-length isoform called "Ml" and a slightly shorter isoform called "M87". M87 is more abundant in both neuronal and non-neuronal tissues.

Figure 3G:
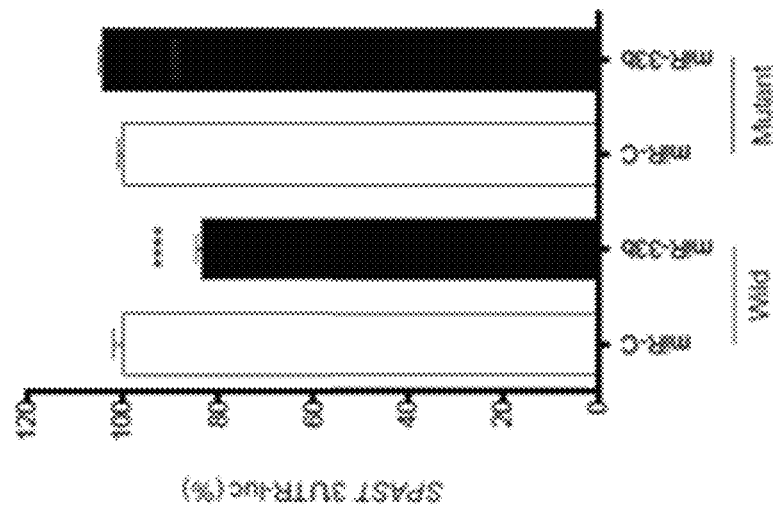
Figure 3F:
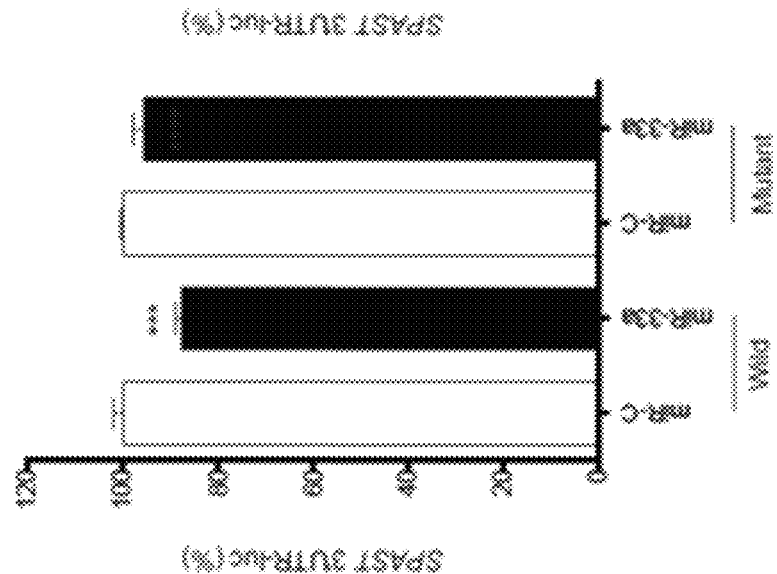
Figure 3F:
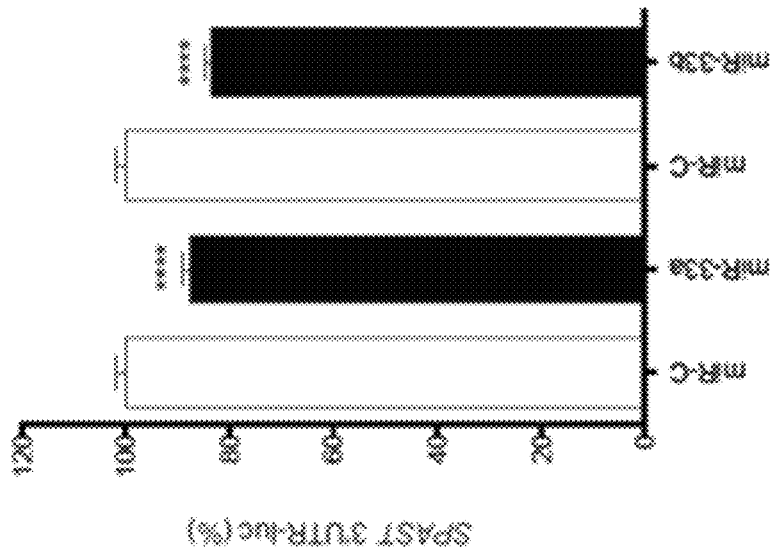

The SPAST 3'-UTR has a potential binding site for miR-33 in mid to large mammals. However, there is no target site in mice (FIG. 3E). To test whether the putative miR-33 target sequence in the SPAST 3'-UTR could mediate translational repression, the present inventors inserted the 3'-UTR of the SPAST transcript into a luciferase expression plasmid (psiCHECK-2-SPAST 3'-UTR) and transfected into HEK 293T cells. CMV-driven miR-33a and miR-33b resulted in decrease in luciferase activity compared with a control vector (miR-control) (FIG. 3F). Mutation in the potential binding site in the 3'-UTR abolished the effect of miR-33 (FIG. 3G).

2-3. Loss of SPASTIN Activity is the Characteristic Phenotype of Hereditary Spastic Paraplegia SPG4 (HSP-SPG4)

Mutations in the SPAST gene (located on 2p22.3) are the most common causes of HSP. Autosomal-dominant HSP-SPG4 in most cases is considered a prototypical HSP with gait impairment due to spasticity and weakness of lower extremities.

Figure 4A:
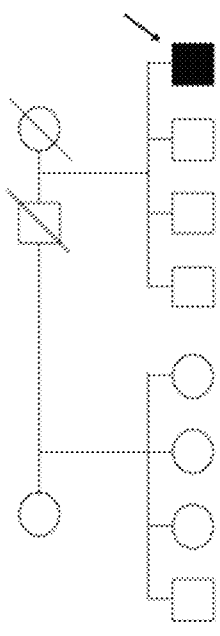
FIGS. 4A-4E show characteristics of SPG4-derived cortical neurons.
Figure 4B:
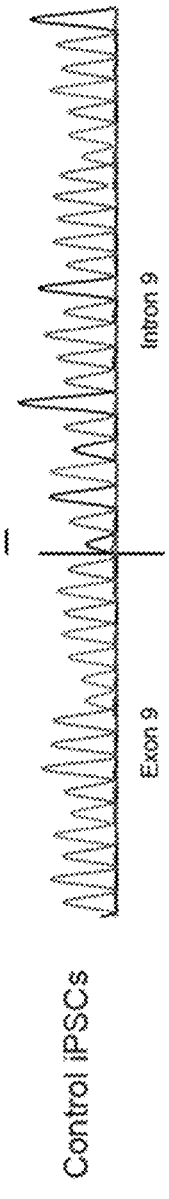
Figure 4B:
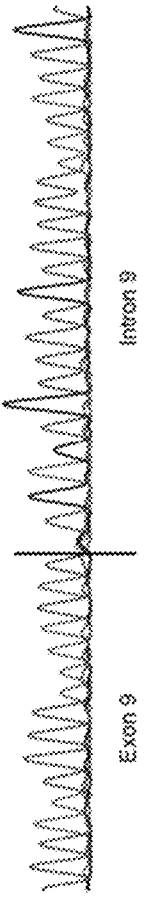
Figure 5A:
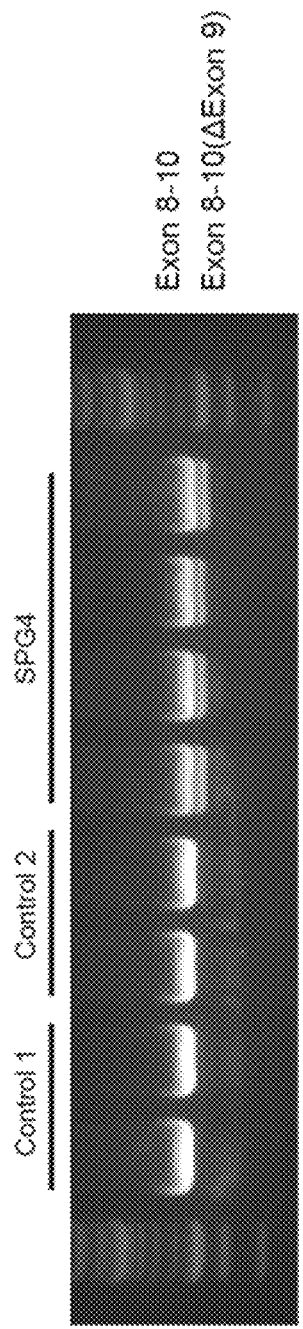
FIG. 5A shows RT-PCR analysis of SPAST in SPG4-iPSCs. A sense primer was designed in exon 8 of SPAST, and an antisense primer was designed in exon 10 of SPAST.
Figure 5B:
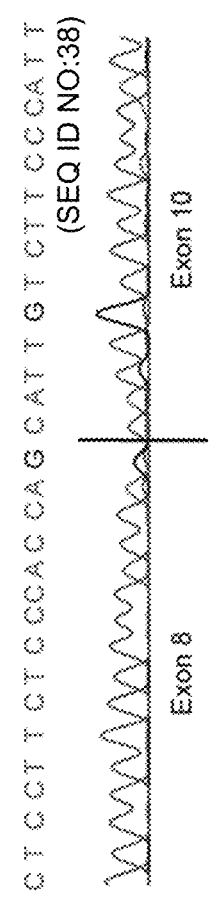
FIG. 5B shows sequencing of an abnormal band (bottom band) in SPG4-iPSCs, indicating skipped exon 9.
Figure 5C:
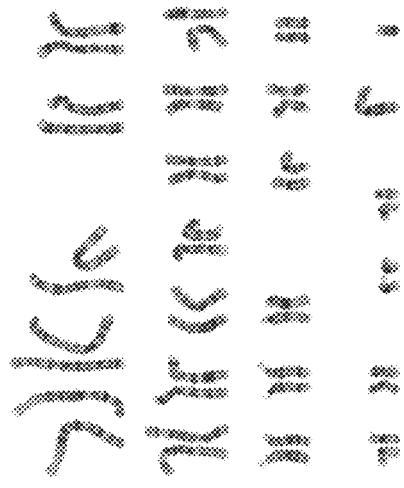
FIG. 5C shows karyotype analysis in SPG4-iPSCs.

Considering the effect of miR-33 in the regulation of SPAST gene in humans, the present inventors hypothesized that inhibition of miR-33 would promote activation of one normal SPAST allele and subsequently reduce the pathological phenotypes. To address this hypothesis, the present inventors generated iPSCs from one SPG4 patient and healthy controls (named "hcl-A" and "hc3-A"). The patient carried the heterozygous G>A substitution located at intron 9 of the SPAST gene that alters the splice site (IVS9+1 G→A), and causes skipping of exon 9. Exon 9 lies within an AAA cassette-encoding region of the gene (pedigree in FIG. 4A). This IVS9+1 G→A mutation in patients with HSP was described previously. This region was sequenced to confirm that the SPG4-derived iPSCs maintained the mutation in the SPAST gene (FIG. 4B and FIGS. 5A and 5B). Chromosomal Q-band analyses showed that these iPSCs from SPG4 had normal karyotypes (FIG. 5C).

Figure 4C:
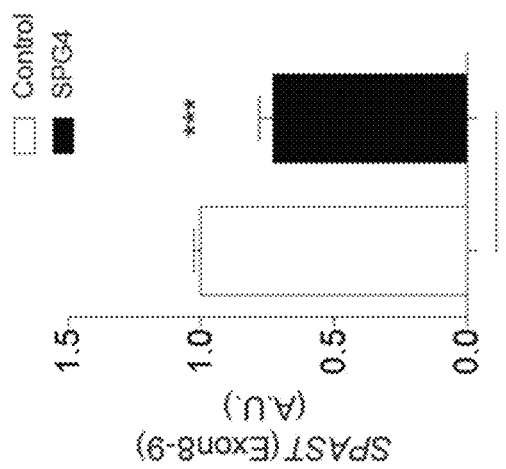
Figure 4D:
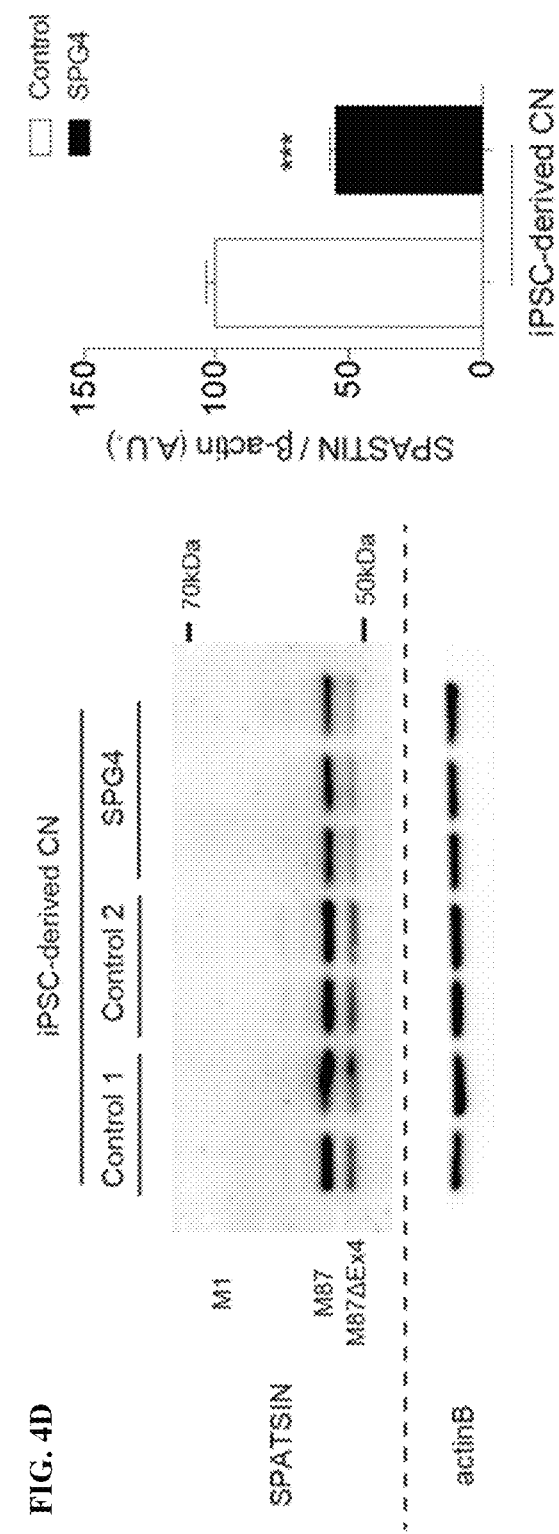

To investigate a cellular phenotype, the present inventors differentiated SPG4 and control iPSCs into cortical neurons by serum-free floating culture of embryoid body-like aggregates with quick reaggregation (SFEBq) as described previously. Since SPG4 is caused by autosomal dominant mutations, SPG4 patients are likely to have about 50% of SPASTIN activity if one allele is nonfunctional. Previous study revealed that neurons derived from an SPG4 patient with splice site mutation show about 50% reduction of SPASTIN protein levels compared to controls. As with the case of this, there was a significant decrease in both SPAST mRNA and SPASTIN protein levels compared to those for controls (FIGS. 4C and 4D).

Figure 4E:
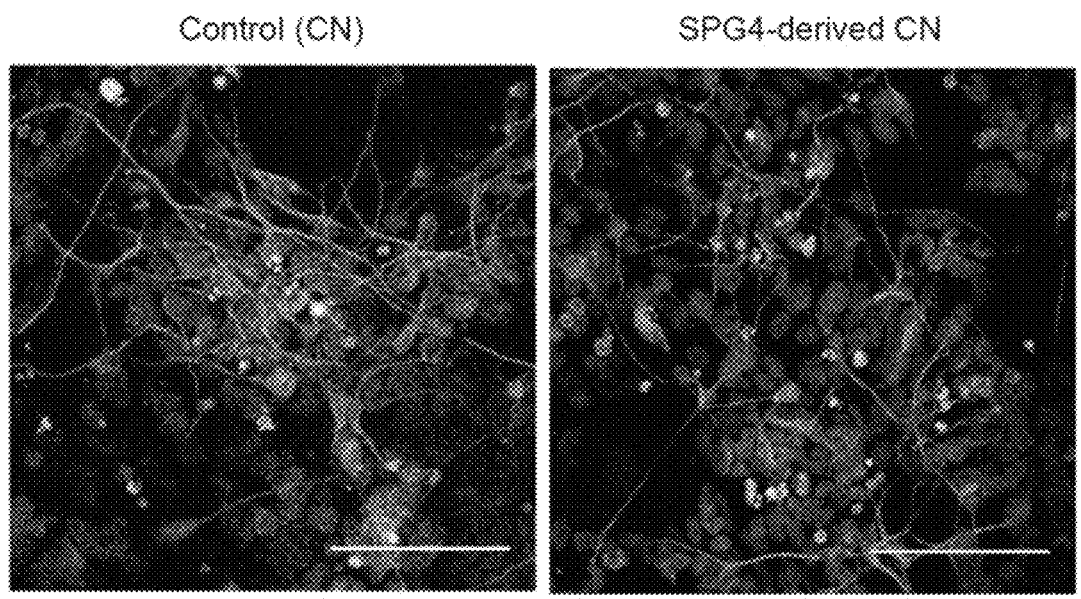
Figure 4E:
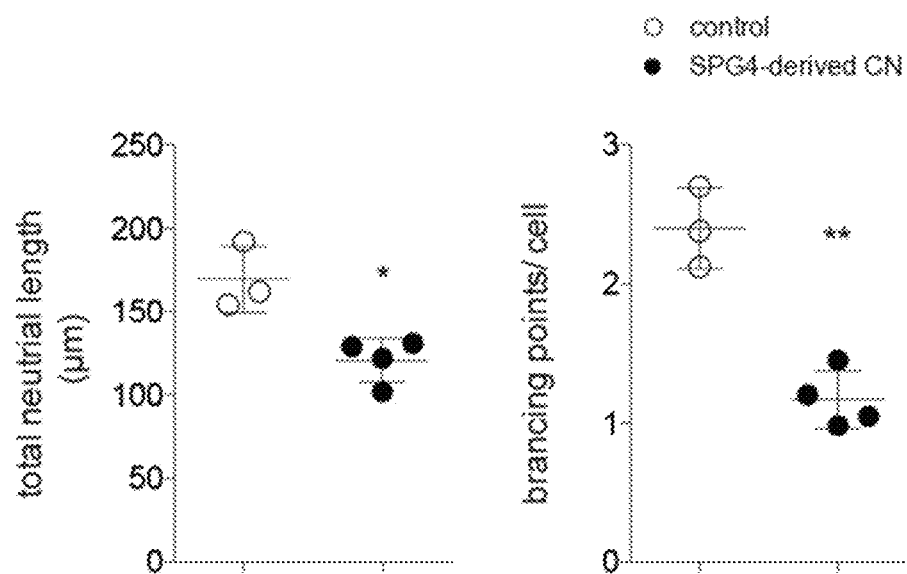

Finally, the present inventors examined SPG4-derived neurite morphology. Immunofluorescent staining revealed that total neurite length and the numbers of branching points were decreased in SPG4-derived cortical neurons (FIG. 4E).

2-4. miR-33 Decreases the Neurite Length of Cortical Neurons Derived from iPSCs Through SPAST 3'UTR Regulation Previous study showed that reduction in SPASTIN levels was directly linked to the observed disease phenotypes and demonstrated that SPG4-derived neurons overexpressing SPASTIN can rescue from neurite outgrowth defects. To determine whether miR-33 directly regulates SPAST expression and affects neural phenotypes in SPG4-derived neurons, the present inventors co-transfected lentiviral constructs to SPG4-derived neurons.

Figures 6A, 6B:
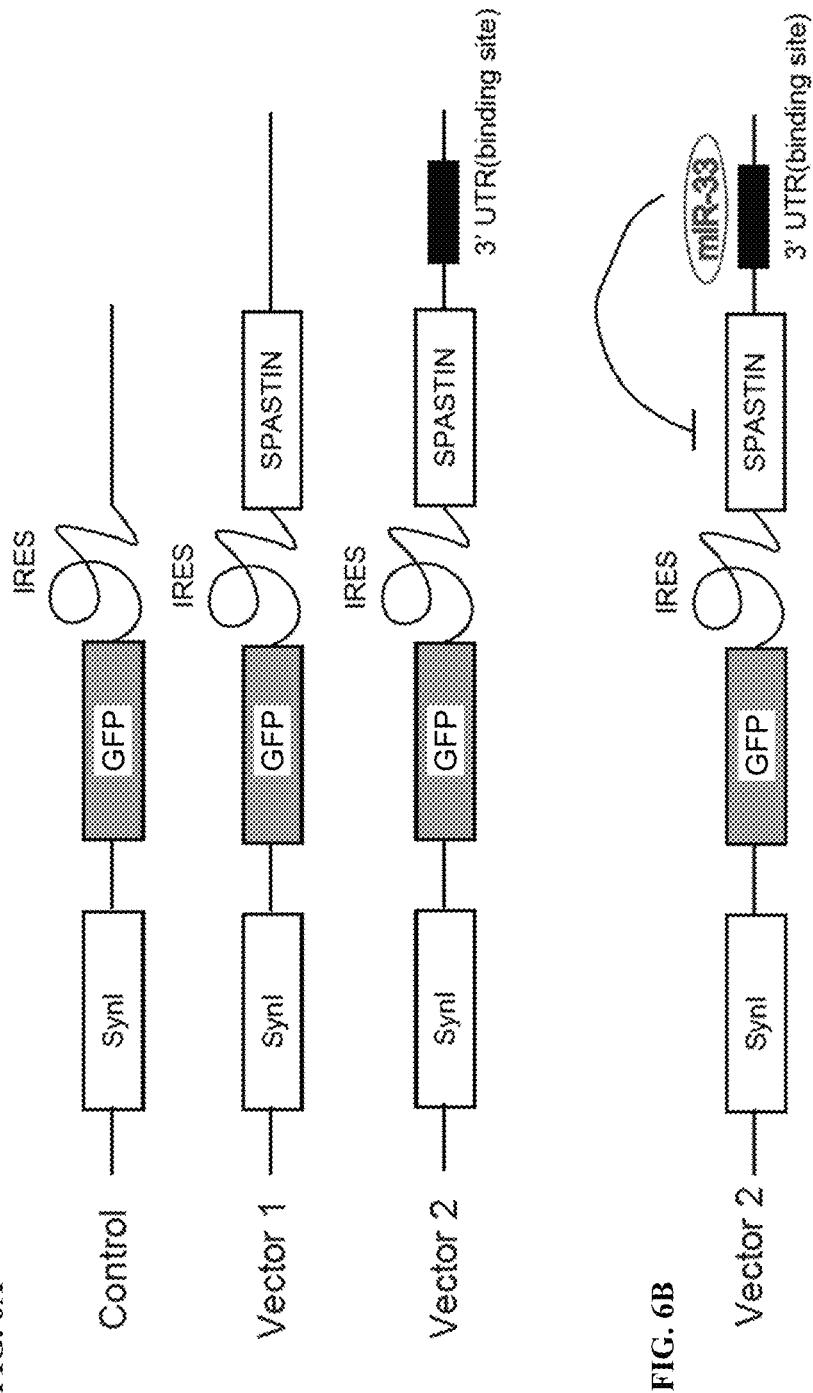
FIG. 6A shows a schematic map showing a lentivirus vector.
FIG. 6B shows a schematic overview of miR-33-mediated translational repression.

The present inventors overexpressed green fluorescent protein (GFP)-internal ribosome entry site (IRES)-SPAST with/without the 3'-UTR including a potential binding site (Vector 1 and Vector 2) in the presence of a synapsin I neuronal driver. The present inventors used GFP-overexpressed SPG4 neurons as a control (FIG. 6A).

Figure 7A:
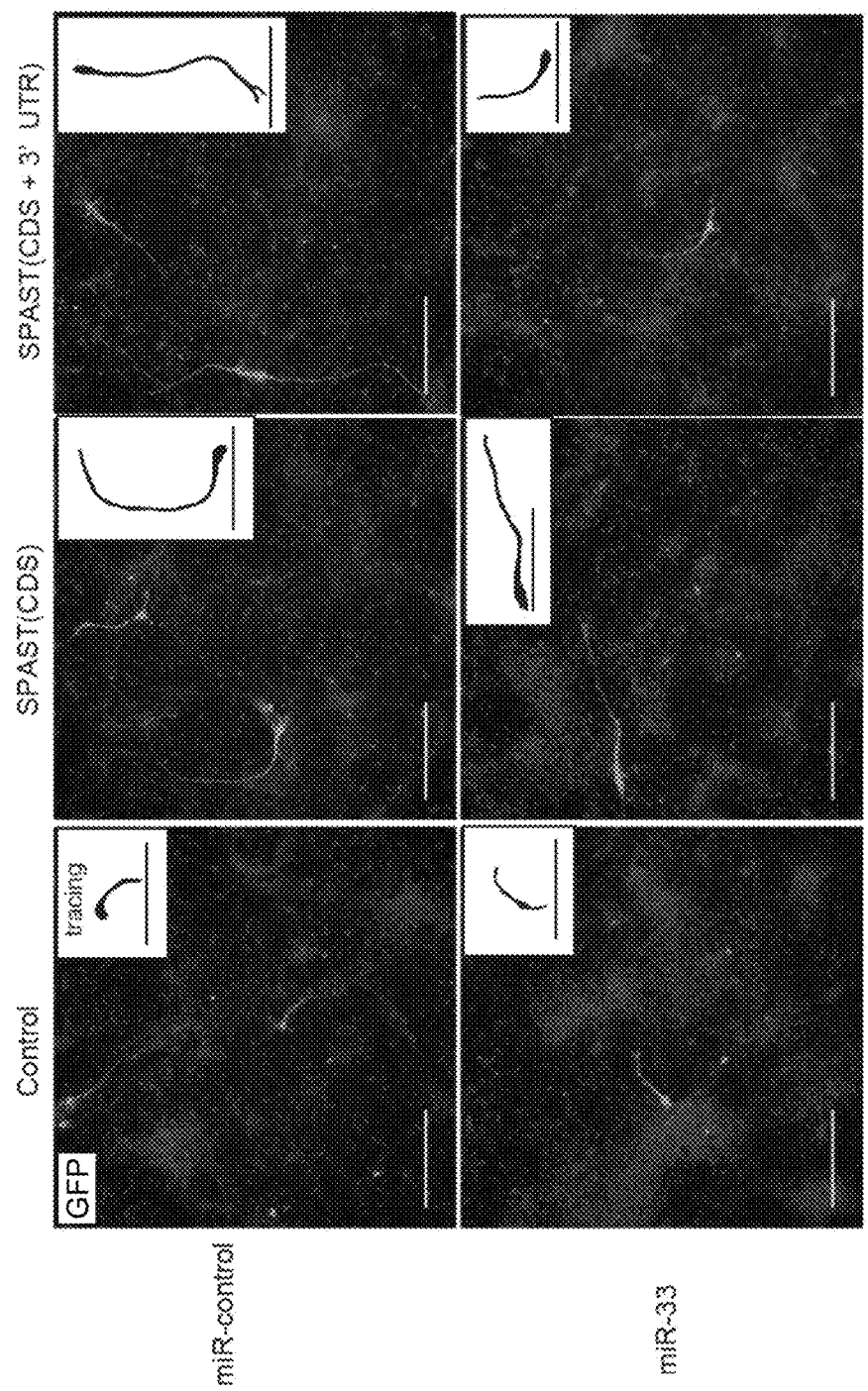
FIGS. 7A and 7B demonstrate that miR-33 affected neural phenotypes in SPG4 though modulating SPAST expression.
Figure 7B:
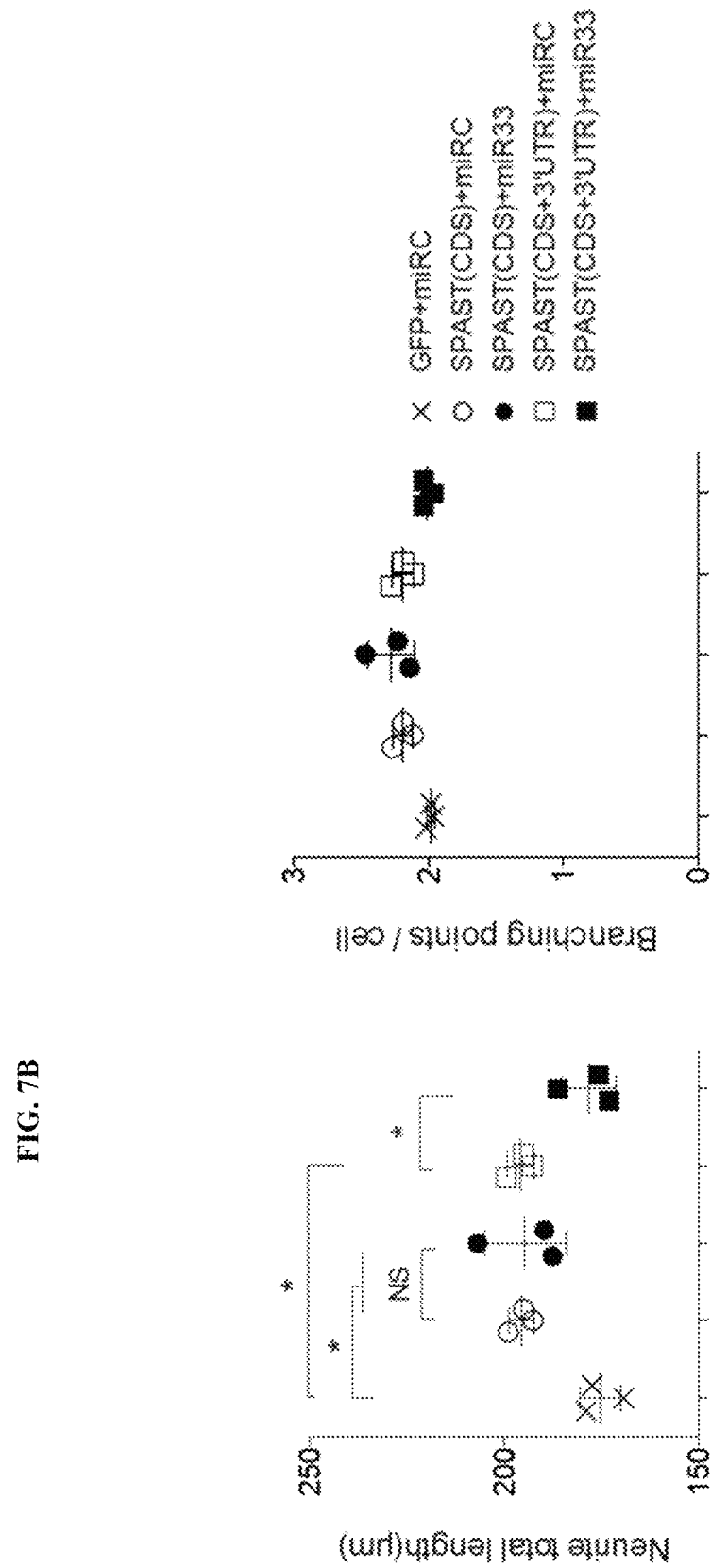

As with the case of previous reports, SPG4-derived neurons overexpressing SPASTIN restored neurite length compared with GFP-control. Co-transfected CMV-driven miR-control with overexpression of either Vector 1 or Vector 2 led to the restoration of neurite length in SPG4-derived neurons. However, co-transfection of CMV-driven miR-33a with Vector 2 decreased the neurite length, which was not observed with Vector 1 (FIGS. 6B, FIGS. 7A and 7B).

2-5. Inhibition of miR-33a Via Locked Nucleic Acid-Anti-miR Ameliorates Neurite Length The present inventors demonstrated that miR-33 modulated the neural phenotypes in SPG4-derived neurons by targeting SPAST 3'-UTR. To investigate whether the inhibition of miR-33 would be a potential therapeutic target for SPG4, SPG4-iPSCs were transfected with LNA-anti-miR-33a (LNA-miR-33a) or a control (LNA-control). The reason for the selection of miR-33a was that the absolute levels of miR-33a were higher than those of miR-33b at both undifferentiated state and neural differentiation (FIG. 8A).

To confirm the knockdown efficiency of LNA-anti-miR-33a, the expression levels of miR-33a were evaluated by RT-PCR 48 hours after transfection. There was about 40% knockdown of miR-33a in iPSC-derived neurons (FIG. 8B).

Down-regulation of miR-33a was associated with up-regulation of ABCA1, which is known as a direct downstream target of miR-33a (FIG. 8C).

Figure 9A:
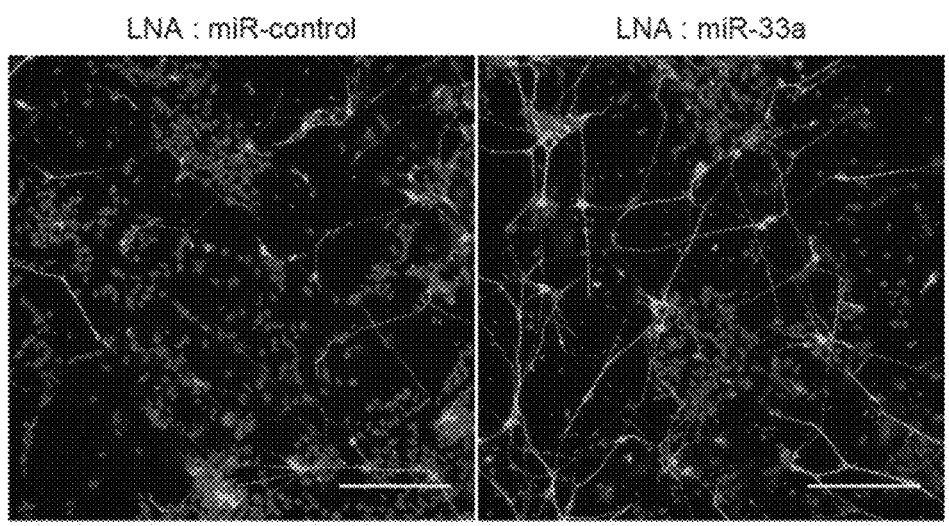
FIGS. 9A and 9B demonstrate that inhibition of miR-33 by LNA restored neurite length in SPG4-derived neurons.
Figure 9B:
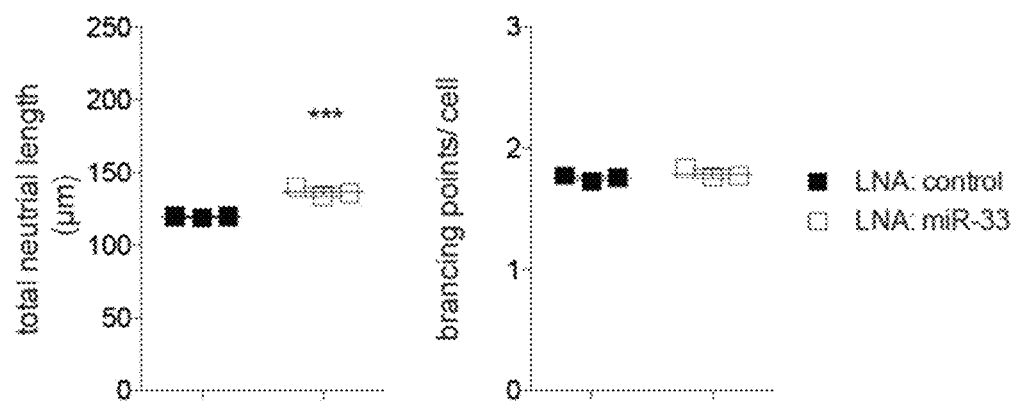

The present inventors observed that neurite length in SPG4-derived neurons was significantly restored 48 hours after transfection with LNA-miR-33a, which suggests the therapeutic potential of miR-33a inhibition for treatment of SPG4 (FIGS. 9A and 9B).

Figure 10A:
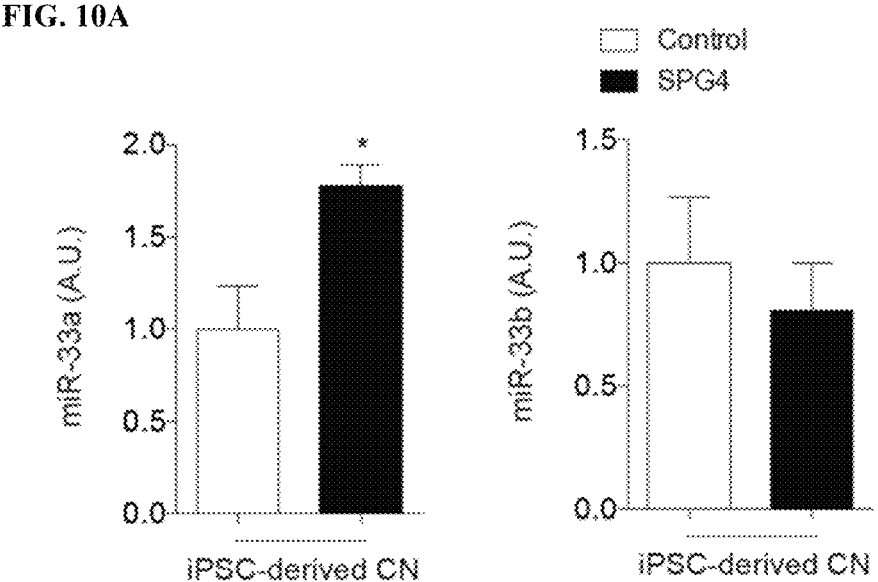
FIG. 10A shows expression levels of miR-33 in SPG4-derived cortical neurons. n=4 to 5 each, *P<0.05 by unpaired t-test.
Figure 10B:
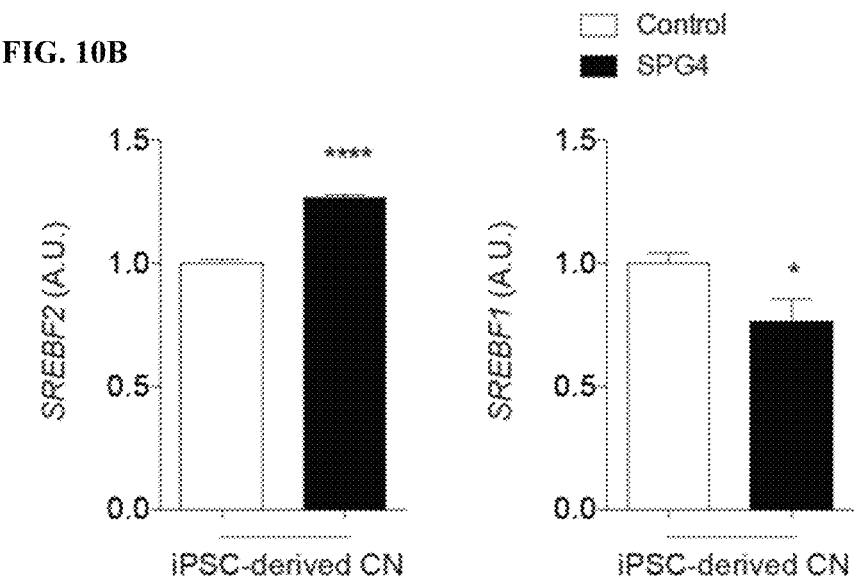
FIG. 10B shows expression levels of SREBF2 and SREBF1 in SPG4-derived cortical neurons. n=4 to 5 each, *P<0.05, **P<0.0001 by unpaired t-test.
Figure 10C:
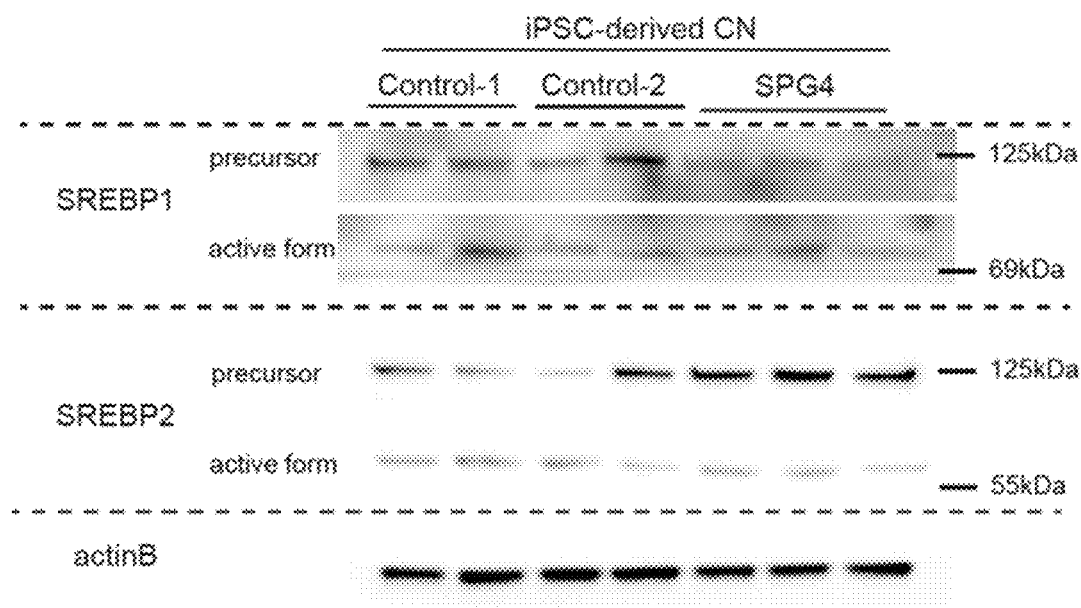
FIG. 10C shows protein levels of SREBP1 and SREBP2 in SPG4-derived cortical neurons.
Figure 10D:
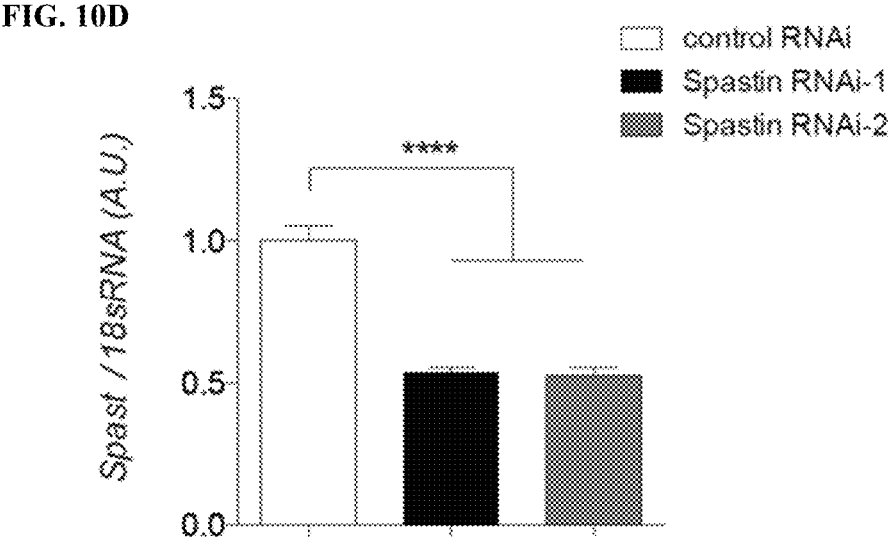
FIG. 10D shows RT-PCR analysis confirming knockdown of spastin in Neuro 2a cells. n=5 each, *P<0.01 by one-way ANOVA.
Figure 10E:
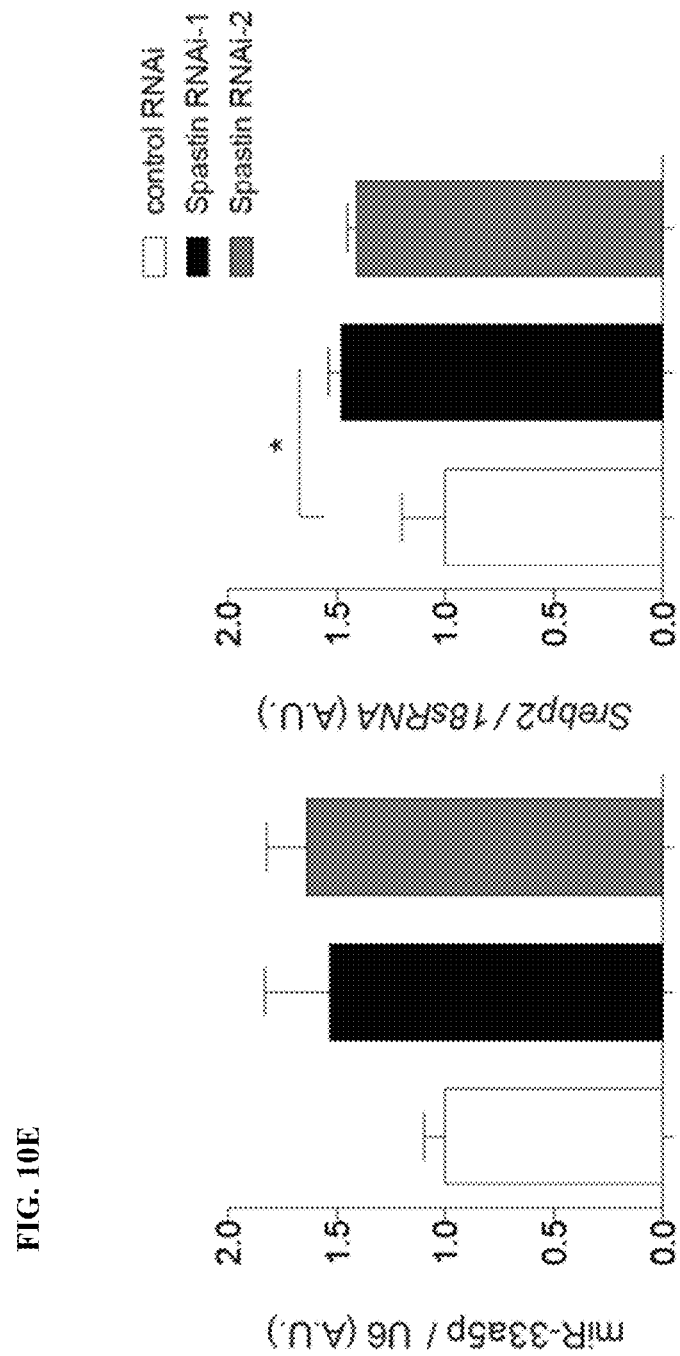
FIG. 10E shows expression levels of miR-33a and Srebp2 in two spastin RNAi Neuro 2a. n=5 each, *P<0.05 by one-way ANOVA.

Moreover, enhanced expression of miR-33a was observed in the SPG4-derived neurons prepared by the present inventors compared with controls, in parallel with host gene mRNA expression and protein levels (FIGS. 10A to 10C). To identify the cause of miR-33a elevation, the present inventors established Spast-knockdown Neuro 2a lines by using lentiviral infection of shRNA constructs. There was about 50% knockdown of Spast mRNA expression in each of the Spast RNAi lines 1 and 2 (FIG. 10D). RT-PCR results revealed that the neuronal cells with reduced spastin as compared to controls tended to increase the expression levels of miR-33a in parallel with the host gene Srebf2 (FIG. 10E). Thus, enhanced expression of miR-33a in the SPG4-derived neurons prepared by the present inventors may be the direct effect of SPASTIN reduction.

3. Discussion

In the previous reports, the roles of miR-33 in mice have been explored, with evidence as regulators of lipid metabolism. However, in humans, they remain unclear because of lack of appropriate models.

In this Example, the present inventors generated miR-33 single (miR-33a or miR-33b) and double (miR-33a and miR-33b) knockout iPSCs by CRISPR-Cas9 and demonstrated complete deletion of mature miR-33 biogenesis in these KO iPSCs. Furthermore, the present inventors identified SPAST as a novel target gene of miR-33 in humans. SPAST, one of responsible genes for hereditary spastic paraplegia, was directly regulated by miR-33. Inhibition of miR-33a by LNA partly reduced the pathological phenotypes of SPG4-derived cortical neurons. It is tempting to speculate that inhibition of miR-33a by synthetic RNA oligoes can promote activation of one normal SPAST allele and subsequently reduce the pathological phenotypes.

Specific and stable knockout for miRNA is essential for studying functions of miRNAs. Genetic knockout of miRNA is the most reliable technique on the study of loss-of-function of miRNA. Recently, the CRISPR-Cas9 technology has been applied to the study of functional genes in a variety of models. In addition, several publications reported that the CRISPR-Cas9 technology could repress miRNA expression by targeting the terminal loop or 5' region of pre-miRNA. In this Example, the present inventors generated miR-33 single and double knockout iPSCs by CRISPR-Cas9 without affecting the expression of their host genes.

Neurodegenerative diseases are largely considered proteinopathies with alternations in the expression levels of genes. Previous studies demonstrated that SPG4-derived neurons had lower numbers of shorter and less branched primary neurites, which is similar to the phenotype observed when human ECS-derived neurons were depleted of SPASTIN by siRNA. In addition, overexpression of SPASTIN in SPG4-derived neurons restores those pathological phenotypes, which suggests that SPG4-phenotype is dependent on SPASTIN dosage. The overwhelming majority of mutations found in HSP-SPG4 patients would abolish microtubule-severing activity of SPASTIN generated from the mutated SPAST allele and theoretically result in accumulation of microtubules that are lower in number but more stable, which leads to nervous system abnormality in development.

In this Example, the present inventors hypothesized that inhibition of miR-33 could increase SPASTIN levels via promoting the transcription of one normal allele and subsequently reduce the pathological phenotypes. To address this hypothesis, the present inventors generated iPSCs from one SPG4 patient and controls. As with the case of previous studies, the present inventors observed that the SPG4-derived neurons prepared by the present inventors, carrying SPAST IVS9+1 G→A mutation, showed impaired neurite length and branching. Moreover, the present inventors observed that co-transfected CMV-driven miR-control with overexpression of SPAST either with or without the 3'UTR including a binding site was sufficient to restore the neurite length and normal branching in SPG4-derived neurons. On the other hand, co-transfected CMV-driven miR-33a with SPAST with the 3'UTR impaired the restoration of the neurite phenotypes, which was not observed in the case of SPAST without the 3'UTR. The data acquired by the present inventors indicated that miR-33a directly regulated SPAST expression and affects neural phenotypes in SPG4-derived neurons.

Several siRNAs, antisense oligonucleotides (ASOs), and LNA are currently under investigation in clinical trials for various diseases. In this Example, the present inventors demonstrated that LNA-based pharmacological inhibition of miR-33a restored neurite length in SPG4-derived cortical neurons. miRNA expression profiling studies were initially done in the field of cancer, and certain miRNAs, including miR-33, have been identified as having tumor-suppressing function or oncogenic potential. Recently, miRNA profile studies identified differentially expressed miRNAs in neurodegenerative diseases, such as Alzheimer disease (AD) and Parkinson disease (PD). The present inventors observed enhanced expression of miR-33a in the SPG4-derived neurons prepared by the present inventors and this may explain the substantial effect of LNA-based inhibition of miR-33a. HSPs are caused by mutations in genes that encode the SPASTIN (SPG4), ATLASTIN-1 (SPG3) and REEP1 (SPG31) proteins. Previous reports showed that these proteins bind one another and form a tubular endoplasmic reticulum network throughout cells and are also involved in lipid droplet formation and enlargement. In addition, recessive forms of HSP genes have been linked to alterations in gene expressions involved in fatty acid metabolism, such as DDHD1 and DDHD2. These data and the experiments conducted by the present inventors with Spast-knockdown Neuro 2a lines suggested that altered lipid metabolism in HSP may have elevated miR-33a in the SPG4-derived neurons prepared by the present inventors.

In summary, the present inventors identified SPAST, one of responsible genes for hereditary spastic paraplegia (HSP-SPG4), as a novel target gene of miR-33 in humans. Inhibition of miR-33a by LNA normalized the pathological phenotypes such as reduction of neurite length of SPG4-derived cortical neurons. The data acquired by the present inventors indicated that miR-33a could be a potential therapy for treatment of SPG4.

4. Method 4-1. Generation of iPSCs and Cell Culture

SPG4 patient iPSCs were generated from peripheral blood mononuclear cells (PBMCs) or T-lymphocytes by using episomal vectors for OCT3/4, Sox2, Klf4, L-Myc, Lin28, and dominant negative p53, or OCT3/4, Sox2, Klf4, L-Myc, Lin28, and p53-shRNA, as previously reported (Okita, K. et al. Stem Cells. 31, 458-466 (2013)), and were cultured on an SNL feeder layer with human iPSC medium (primate embryonic stem cell medium; ReproCELL Inc., Yokohama, Japan) supplemented with 4 ng/ml basic fibroblast growth factor (FGF; Wako Pure Chemical Industries, Ltd., Osaka, Japan) and penicillin/streptomycin.

4-2. Construction of Plasmids for Gene Targeting

For CRISPR-Cas9n plasmids, guide RNAs were designed by using CRISPR Design (crispr.mit.edu/). The guide RNA oligonucleotides (Table 1) were inserted into a pHL-HaccdB plasmid. For constructing a donor plasmid, the present inventors modified pBluescript SK (+) by inserting the selection cassette and fragments of genomic sequences 5' and 3' amplified by PCR. Each homologous arm was bound by using an In-Fusion HD cloning kit (Clontech Laboratories, Inc., Mountain View, Calif.) as 5' and 3' homology arms.

4-3. Genome Editing of iPSCs by Gene Targeting

For transfection of CRISPR-Cas9n, $1 \times 10^6$ iPSCs were electroporated with 3 µg of each of two gRNA plasmids, 5 µg of a Cas9n (D10A Cas9) plasmid, and 10 µg of a donor plasmid by using a NEPA21 electroporator (Nepa Gene Co., Ltd., Chiba, Japan). Transfected cells were plated onto feeder cells and cultured in human ES medium supplemented with 10 µM of Y-27632 for 1 day. Three days after transfection, neomycin and/or puromycin selection was applied and continued for 10 days. Resistant colonies were picked out and expanded for genomic DNA extraction and PCR screening. To remove the selection cassette, cells were transiently transfected with a Cre recombinase-expressing plasmid (pCXW-Cre-euro) by electroporation, and puromycin-resistant colonies were selected. Selection cassette excision and bi-allelic deletion for miR-33a and/or miR-33b were confirmed by genomic PCR screening and Sanger sequence analysis.

4-4. Induction of Cortical Neuron Differentiation

Human iPSCs were dissociated to single cells and quickly reaggregated in U-bottom 96-well plates for suspension culture (Greiner Bio-One International GmbH, Frick-enhausen, Germany), pre-coated with 2% Pluronic (Sigma-Aldrich Co. LLC, St. Louis, Mo.) in 100% ethanol. Aggregations of embryoid bodies (EBs) were cultured in 5% DFK medium (Dulbecco's modified Eagle's medium/Ham's F12 (Sigma-Aldrich Co. LLC), 5% KSR (Gibco, Waltham, Mass.), NEAA (Invitrogen), L-glutamine (Sigma-Aldrich Co. LLC), 0.1 M 2-mercaptoethanol (Invitrogen) with or without 2 µM dorsomorphin and 10 µM SB431542 (Wako Pure Chemical Industries, Ltd.) in the neural inductive stage (day 0 to 8). After induction, EBs were transferred onto Matrigel (Becton, Dickinson and Company)-coated 6-well culture plates and cultured with 1×N2 supplement (Invitrogen), 2 µM dorsomorphin, and 10 µM SB431542 supplemented in the patterning stage (day 8 to 24). After the patterning stage, migrated neural precursor cells were separated from the plate bottom by using Accutase (Innovative Cell Technologies, Inc.) and cultured in Neurobasal medium FULL, Neurobasal medium (Invitrogen/Gibco) supplemented with 1×B27 without vitamin A (Invitrogen/Gibco), 1× Glutamax (Invitrogen/Gibco), 10 ng/ml BDNF, 10 ng/ml GDNF, and 10 ng/ml NT-3 on matrigel-coated 12-well or 24-well culture plates or a coverslip in the neural maturation stage, and then cultured until experiments.

4-5. Western Blotting

Western blotting was performed by using standard procedures as described previously. Samples were dissolved in lysis buffer consisting of 100 mM Tris-HCl, pH 7.4, 75 mM NaCl, and 1% Triton X-100 (NACALAI TESQUE, INC.). The lysis buffer was supplemented with complete mini protease inhibitor (F. Hoffmann-La Roche Ltd.), ALLN (25 µg ml-1), 0.5 mM NaF, and 10 mM $Na_3VO_4$ just before use. The protein concentration was determined by using a bicinchoninic acid (BCA) protein assay kit (Bio-Rad Laboratories, Inc.). All samples (10 µg of protein) were suspended in lysis buffer, fractionated by using NuPAGE 4-12% Bis-Tris (Invitrogen) gels, and transferred to a Protran nitrocellulose transfer membrane (Whatman). The membrane was blocked by using 1× phosphate-buffered saline (PBS) containing 5% non-fat milk for 1 hour and incubated with primary antibodies against SPASTIN (S7074, Sigma-Aldrich Co. LLC), against ABCA1 (NB400-105, Novus Biologicals), against SREBP-1 (2A4, Santa Cruz Biotechnology, Inc.), against SREBP-2 (Cayman Chemical Company), against TF2B (EP4588, Abcam), and against β actin (C4, Santa Cruz Biotechnology, Inc.) overnight at 4° C. Following a washing step in PBS-0.05% Tween 20 (0.05% T-PBS), the membrane was incubated with a secondary antibody (anti-rabbit or anti-mouse IgG HRP-linked; 1:2,000) for 1 hour at room temperature. The membrane was then washed in 0.05% T-PBS and subjected to detection by ECL Western Blotting Detection Reagent (GE Healthcare), with an LAS-4000 system (GE Healthcare Life Sciences).

4-6. RNA Extraction and qPT-PCR

Total RNA was isolated and purified by using TriPure Isolation Reagent (F. Hoffmann-La Roche Ltd.), and cDNA was synthesized from 100 ng of total RNA by using a Transcriptor First Strand cDNA Synthesis Kit (F. Hoffmann-La Roche Ltd.) in accordance with the manufacturer's instructions. For quantitative RT-PCR, specific genes were amplified by 40 cycles using SYBR Green PCR Master Mix (Applied Biosystems). Expression was normalized to the housekeeping gene 18S ribosomal RNA. Gene-specific primers are listed in Table 2.

TABLE 2

Table 2. Primer sequences
Gene-specific oligonucleotide primer sequences used

| Gene | Species | Forward | Reverse |
| --- | --- | --- | --- |
| SREBF1 | Human | AACAGTCCCACTGGTCGTAGAT (SEQ ID NO: 6) | TGTTGCAGAAAGCGAATGTAGT (SEQ ID NO: 7) |
| SREBF2 | Human | AGGAGAACATGGTGCTGA (SEQ ID NO: 8) | TAAAGGAGAGGCACAGGA (SEQ ID NO: 9) |
| SPAST | Human | AGCTGGTCAAGACTTGGCAA (SEQ ID NO: 10) | AGGTTGCATTCGATTCTGCA (SEQ ID NO: 11) |
| ABCA1 | Human | GTCCTCTTTCCCGCATTATCTGG (SEQ ID NO: 12) | AGTTCCTGGAAGGTCTTGTTCAC (SEQ ID NO: 13) |
| 18S | Human | AGAAACGGCTACCACATCCA (SEQ ID NO: 14) | CCCTCCAATGGATCCTCGTT (SEQ ID NO: 15) |
| Srebf2 | Mouse | GTGGAGCAGTCTCAACGTCA (SEQ ID NO: 16) | TGGTAGGTCTCACCCAGGAG (SEQ ID NO: 17) |
| Spast | Mouse | CGGGCCAAGGTGAACAGTAT (SEQ ID NO: 18) | GATGTCCATTGCGGCATGTC (SEQ ID NO: 19) |
| 18S | Mouse | CGCGGTTCTATTTTGTTGGT (SEQ ID NO: 20) | AGTCGGCATCGTTTATGGTC (SEQ ID NO: 21) |

4-7. Quantitative PCR for miRNA

Total RNA was isolated by using TriPure Isolation Reagent (F. Hoffmann-La Roche Ltd.). miR-33 was measured in accordance with the TaqMan MicroRNA assays (Applied Biosystems) protocol, and the products were analyzed by using a thermal cycler (ABI Prism7900HT sequence detection system). Samples were normalized by U6 snRNA expression. The present inventors also measured 16 pM, 4 pM, 1 pM, 250 fM, 62.5 fM, and 15.625 fM oligonucleotides of miR-33a and miR-33b, and created a calibration curve. The present inventors calculated the absorbance value of each sample to figure out its concentration.

4-8. Dual Luciferase Assays

Full length PCR fragments of the 3'-UTR of SPAST were amplified from human iPSC cDNAs and subcloned in a psi-CHECK2-let-7 8X vector (addgene). To create WT or mutant 3'-UTR luciferase reporter genes, a fragment of the SPAST3'-UTR as follows was inserted into a psi-CHECK2-let-7 8X vector:

Wild type: acagacttaaacaaaatatacaatgcaaatgtaattttttgttgtt-taag (SEQ ID NO: 22)

Mutant: acagacttaaacaaaatatacCCGTAaaatgtaattttttgttgtt-taag (SEQ ID NO: 23)

Luciferase activities were measured as described previously.

4-9. SPASTIN and GFP Overexpression

Human SPAST, with or without full length 3'-UTR of SPAST, was cloned from human iPSCs and inserted into a pCMV-IRES-GFP vector, and then the CMV promoter was replaced with a Synapsin I promoter, which is relatively neuron-specific. The present inventors produced lentiviral stocks in 293FT cells in accordance with the manufacturer's protocol (Invitrogen). In brief, virus-containing medium was collected 48 hours after transfection and filtered through a 0.45-μm filter. Cells were infected with SPAST, SPAST with 3'-UTR, or an empty GFP control lentivirus. Neural cultures were allowed to differentiate for 10 days after DNA transduction. Infected cells were highlighted with GFP.

4-10. Cell Transfection with LNA-Anti-miR-33

Cells were transfected with 10 nM LNA-anti-miR-33 or LNA-control by using Lipofectamine RNAiMAX (Invitrogen) according to the manufacturer's instructions. The cells were used for analysis 48 hours after transfection.

LNA-anti-miR-33 is a nucleic acid having the following sequence:

A(L)^a^5(L)^t^A(L)^c^A(L)^a^T(L)^g^5(L)^a (SEQ ID NO: 24)

LNA-control is a nucleic acid having the following sequence:

A(L)^a^5(L)^a^A(L)^t^A(L)^c^T(L)^a^5(L)^g (SEQ ID NO: 25)

(Rule of symbols) N(L)=LNA, 5(L)=LNA_mC (5-methylcytosine), ^=phosphorothioate bond 4-11. Immunocytochemistry Cells were fixed in 4% paraformaldehyde (pH 7.4) for 30 minutes at room temperature and rinsed with PBS. The cells were subjected to permeabilization in PBS containing 0.2% Triton-X 100 for 10 minutes at room temperature, followed by rinsing with PBS. Nonspecific binding was blocked with Block Ace (DS pharma biomedical Co., Ltd.) for 60 minutes at room temperature. The cells were incubated with primary antibodies overnight at 4° C., and then labeled with appropriate fluorescent-tagged secondary antibodies. DAPI (DOJINDO LABORATORIES) was used to label nuclei. The following primary antibody was used in immunocytochemistry: βIII tubulin (1:1000, CST, 5568S). For evaluating the positive count ratio of immunocytochemistry, the present inventors imaged the cells by using automated microscopy by ArrayScan and counted the immunostained structures by using HCS Studio 2.0 Cell Analysis Software (Thermo Fisher Scientific).

4-12. Statistical Analysis

Data are presented as mean±standard error of the mean (SEM). Statistical comparisons were performed by using unpaired t-test or one-way analysis of variance (ANOVA) with Sidak's post-hoc test (three or more groups) as indicated in the figure legends. Statistical analyses were performed by using GraphPad Prism 6 (GraphPad Software, Inc.) with p values of <0.05 considered as being statistically significant.

INDUSTRIAL APPLICABILITY

The present invention enables direct treatment of a neurodegenerative disease such as HSP-SPG4.

All of the publications, patents, and patent applications cited herein are directly incorporated herein by reference.

The invention claimed is:

1. A miR-33a function inhibitor comprising, as an active ingredient, an antisense oligonucleotide that consists of a nucleotide sequence set forth in SEQ ID NO: 24, and wherein each internucleotide bond in the nucleotide sequence is a phosphorothioate bond.

2. A composition for treating hereditary spastic paraplegia SPG4, the composition comprising, as an active ingredient, an antisense oligonucleotide that consists of a nucleotide sequence set forth in SEQ ID NO: 24, and wherein each internucleotide bond in the nucleotide sequence is a phosphorothioate bond.

3. A method for treating hereditary spastic paraplegia SPG4, the method comprising administering to a subject an antisense oligonucleotide that consists of a nucleotide sequence set forth in SEQ ID NO: 24 wherein each internucleotide bond in the nucleotide sequence is a phosphorothioate bond.

* * * * *

SEQUENCE LISTING

```
<160> NUMBER OF SEQ ID NOS: 38

<210> SEQ ID NO 1
<211> LENGTH: 21
<212> TYPE: RNA
<213> ORGANISM: Homo sapiens

<400> SEQUENCE: 1
gugcauugua guugcauugc a                                              21

<210> SEQ ID NO 2
<211> LENGTH: 23
<212> TYPE: DNA
<213> ORGANISM: Artificial
<220> FEATURE:
<223> OTHER INFORMATION: DNA encoding CRISPR guide RNA

<400> SEQUENCE: 2
gctgcccgcc aggaggtatg cgg                                            23

<210> SEQ ID NO 3
<211> LENGTH: 23
<212> TYPE: DNA
<213> ORGANISM: Artificial
<220> FEATURE:
<223> OTHER INFORMATION: DNA encoding CRISPR guide RNA

<400> SEQUENCE: 3
tgtagttgca ttgcatgttc tgg                                            23

<210> SEQ ID NO 4
<211> LENGTH: 20
<212> TYPE: DNA
<213> ORGANISM: Artificial
<220> FEATURE:
<223> OTHER INFORMATION: DNA encoding CRISPR guide RNA

<400> SEQUENCE: 4
tgcaacagca atgcaccgcg                                                20

<210> SEQ ID NO 5
<211> LENGTH: 20
<212> TYPE: DNA
<213> ORGANISM: Artificial
<220> FEATURE:
<223> OTHER INFORMATION: DNA encoding CRISPR guide RNA

<400> SEQUENCE: 5
tcggcagtgc agcccggagc                                                20

<210> SEQ ID NO 6
<211> LENGTH: 22
<212> TYPE: DNA
<213> ORGANISM: Artificial
<220> FEATURE:
<223> OTHER INFORMATION: Primer

<400> SEQUENCE: 6
aacagtccca ctggtcgtag at                                             22
```

<210> SEQ ID NO 7
<211> LENGTH: 22
<212> TYPE: DNA
<213> ORGANISM: Artificial
<220> FEATURE:
<223> OTHER INFORMATION: Primer

<400> SEQUENCE: 7
tgttgcagaa agcgaatgta gt                                              22

<210> SEQ ID NO 8
<211> LENGTH: 18
<212> TYPE: DNA
<213> ORGANISM: Artificial
<220> FEATURE:
<223> OTHER INFORMATION: Primer

<400> SEQUENCE: 8
aggagaacat ggtgctga                                                   18

<210> SEQ ID NO 9
<211> LENGTH: 18
<212> TYPE: DNA
<213> ORGANISM: Artificial
<220> FEATURE:
<223> OTHER INFORMATION: Primer

<400> SEQUENCE: 9
taaaggagag gcacagga                                                   18

<210> SEQ ID NO 10
<211> LENGTH: 20
<212> TYPE: DNA
<213> ORGANISM: Artificial
<220> FEATURE:
<223> OTHER INFORMATION: Primer

<400> SEQUENCE: 10
agctggtcaa gacttggcaa                                                 20

<210> SEQ ID NO 11
<211> LENGTH: 20
<212> TYPE: DNA
<213> ORGANISM: Artificial
<220> FEATURE:
<223> OTHER INFORMATION: Primer

<400> SEQUENCE: 11
aggttgcatt cgattctgca                                                 20

<210> SEQ ID NO 12
<211> LENGTH: 23
<212> TYPE: DNA
<213> ORGANISM: Artificial
<220> FEATURE:
<223> OTHER INFORMATION: Primer

<400> SEQUENCE: 12
gtcctctttc ccgcattatc tgg                                             23

<210> SEQ ID NO 13
<211> LENGTH: 23
<212> TYPE: DNA
<213> ORGANISM: Artificial
<220> FEATURE:

<223> OTHER INFORMATION: Primer

<400> SEQUENCE: 13
agttcctgga aggtcttgtt cac                                           23

<210> SEQ ID NO 14
<211> LENGTH: 20
<212> TYPE: DNA
<213> ORGANISM: Artificial
<220> FEATURE:
<223> OTHER INFORMATION: Primer

<400> SEQUENCE: 14
agaaacggct accacatcca                                               20

<210> SEQ ID NO 15
<211> LENGTH: 20
<212> TYPE: DNA
<213> ORGANISM: Artificial
<220> FEATURE:
<223> OTHER INFORMATION: Primer

<400> SEQUENCE: 15
ccctccaatg gatcctcgtt                                               20

<210> SEQ ID NO 16
<211> LENGTH: 20
<212> TYPE: DNA
<213> ORGANISM: Artificial
<220> FEATURE:
<223> OTHER INFORMATION: Primer

<400> SEQUENCE: 16
gtggagcagt ctcaacgtca                                               20

<210> SEQ ID NO 17
<211> LENGTH: 20
<212> TYPE: DNA
<213> ORGANISM: Artificial
<220> FEATURE:
<223> OTHER INFORMATION: Primer

<400> SEQUENCE: 17
tggtaggtct cacccaggag                                               20

<210> SEQ ID NO 18
<211> LENGTH: 20
<212> TYPE: DNA
<213> ORGANISM: Artificial
<220> FEATURE:
<223> OTHER INFORMATION: Primer

<400> SEQUENCE: 18
cgggccaagg tgaacagtat                                               20

<210> SEQ ID NO 19
<211> LENGTH: 20
<212> TYPE: DNA
<213> ORGANISM: Artificial
<220> FEATURE:
<223> OTHER INFORMATION: Primer

<400> SEQUENCE: 19
gatgtccatt gcggcatgtc                                               20

```
<210> SEQ ID NO 20
<211> LENGTH: 20
<212> TYPE: DNA
<213> ORGANISM: Artificial
<220> FEATURE:
<223> OTHER INFORMATION: Primer

<400> SEQUENCE: 20
cgcggttcta ttttgttggt                                               20

<210> SEQ ID NO 21
<211> LENGTH: 20
<212> TYPE: DNA
<213> ORGANISM: Artificial
<220> FEATURE:
<223> OTHER INFORMATION: Primer

<400> SEQUENCE: 21
agtcggcatc gtttatggtc                                               20

<210> SEQ ID NO 22
<211> LENGTH: 50
<212> TYPE: DNA
<213> ORGANISM: Homo sapiens

<400> SEQUENCE: 22
acagacttaa acaaaatata caatgcaaat gtaatttttt gttgtttaag              50

<210> SEQ ID NO 23
<211> LENGTH: 50
<212> TYPE: DNA
<213> ORGANISM: Artificial
<220> FEATURE:
<223> OTHER INFORMATION: Mutant of SPAST 3'UTR fragment

<400> SEQUENCE: 23
acagacttaa acaaaatata cccgtaaaat gtaatttttt gttgtttaag              50

<210> SEQ ID NO 24
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (5)..(5), (7)..(7), (9)..(9)
<223> OTHER INFORMATION: LNA
<220> FEATURE:
<221> NAME/KEY: misc_feature
<222> LOCATION: (3)..(3), (11)..(11)
<223> OTHER INFORMATION: 5-methylcytosine LNA

<400> SEQUENCE: 24
aactacaatg ca                                                       12

<210> SEQ ID NO 25
<211> LENGTH: 12
<212> TYPE: DNA
<213> ORGANISM: Artificial
<220> FEATURE:
<223> OTHER INFORMATION: Synthetic
<220> FEATURE:
<221> NAME/KEY: misc_feature
<222> LOCATION: (1)..(1), (5)..(5), (7)..(7), (9)..(9)
<223> OTHER INFORMATION: LNA
<220> FEATURE:
<221> NAME/KEY: misc_feature
<222> LOCATION: (3)..(3), (11)..(11)
```

```
<223> OTHER INFORMATION: 5-methylcytosine LNA

<400> SEQUENCE: 25
aacaatacta cg                                                           12

<210> SEQ ID NO 26
<211> LENGTH: 114
<212> TYPE: DNA
<213> ORGANISM: Artificial
<220> FEATURE:
<223> OTHER INFORMATION: premiR-33a without seed sequence

<400> SEQUENCE: 26
ctgtggcgca acgcaattag tgataacttc gtatagcata cattatacga agttatgttt      60
gttaccattt gtgttctaat ggtacccatg caatgtttcc acagtgcatc acag           114

<210> SEQ ID NO 27
<211> LENGTH: 87
<212> TYPE: DNA
<213> ORGANISM: Artificial
<220> FEATURE:
<223> OTHER INFORMATION: premiR-33b without seed sequence

<400> SEQUENCE: 27
gcgggcgggc gcaacgcaat tagtgataac ttcgtatagc atacattata cgaagttatg      60
tttgttacca tttgcccctg gcaccac                                          87

<210> SEQ ID NO 28
<211> LENGTH: 24
<212> TYPE: DNA
<213> ORGANISM: Homo sapiens

<400> SEQUENCE: 28
tgccctcaac cacgtggtcc agct                                              24

<210> SEQ ID NO 29
<211> LENGTH: 25
<212> TYPE: DNA
<213> ORGANISM: Homo sapiens

<400> SEQUENCE: 29
tccattgaca aggccgtgca gctgt                                             25

<210> SEQ ID NO 30
<211> LENGTH: 39
<212> TYPE: RNA
<213> ORGANISM: Homo sapiens

<400> SEQUENCE: 30
aaaacagacu uaaacaaaau auacaaugca aauguaauu                              39

<210> SEQ ID NO 31
<211> LENGTH: 39
<212> TYPE: RNA
<213> ORGANISM: Pan troglodytes

<400> SEQUENCE: 31
aaaacaaacu uaaacaaaau auacaaugca aauggaauu                              39

<210> SEQ ID NO 32
<211> LENGTH: 39
<212> TYPE: RNA
<213> ORGANISM: Macaca mulatta
```

```
<400> SEQUENCE: 32
aaaacaaacu uaaacaaaau auacaaugca aauagaauu                              39

<210> SEQ ID NO 33
<211> LENGTH: 39
<212> TYPE: RNA
<213> ORGANISM: Canis lupus familiaris

<400> SEQUENCE: 33
aaaacaaauu uaaauaaaau auacaaugca aauggagua                              39

<210> SEQ ID NO 34
<211> LENGTH: 39
<212> TYPE: RNA
<213> ORGANISM: Bos taurus

<400> SEQUENCE: 34
aaaauaaauu uaaauaaagu auacaaugca aauggaaua                              39

<210> SEQ ID NO 35
<211> LENGTH: 37
<212> TYPE: RNA
<213> ORGANISM: Mus musculus

<400> SEQUENCE: 35
aagacagacc uaaauaaaau augcaauaug aauggaa                                37

<210> SEQ ID NO 36
<211> LENGTH: 40
<212> TYPE: DNA
<213> ORGANISM: Homo sapiens

<400> SEQUENCE: 36
tttaacttca aaatacgtga gtgctctgtt tccaatattg                             40

<210> SEQ ID NO 37
<211> LENGTH: 40
<212> TYPE: DNA
<213> ORGANISM: Homo sapiens

<400> SEQUENCE: 37
tttaacttca aaatacatga gtgctctgtt tccaatattg                             40

<210> SEQ ID NO 38
<211> LENGTH: 31
<212> TYPE: DNA
<213> ORGANISM: Homo sapiens

<400> SEQUENCE: 38
ctccttctcc caccagcatt gtcttcccat t                                      31
```